United States Patent
Sakai et al.

(10) Patent No.: US 9,857,380 B2
(45) Date of Patent: Jan. 2, 2018

(54) PROFILING FRAGMENTS OF ELASTIC FIBERS AND MICROFIBRILS AS BIOMARKERS FOR DISEASE

(75) Inventors: Lynn Y. Sakai, Portland, OR (US); Lynn M. Marshall, Portland, OR (US); Eric J. Carlson, Portland, OR (US); Noe L. Charbonneau, Portland, OR (US); Susan J. Hayflick, Portland, OR (US)

(73) Assignee: SHRINERS HOSPITAL FOR CHILDREN, Tampa, FL (US)

( * ) Notice: Subject to any disclaimer, the term of this patent is extended or adjusted under 35 U.S.C. 154(b) by 875 days.

(21) Appl. No.: 13/280,644

(22) Filed: Oct. 25, 2011

(65) Prior Publication Data

US 2012/0174244 A1 Jul. 5, 2012

Related U.S. Application Data

(63) Continuation of application No. PCT/US2010/032551, filed on Apr. 27, 2010.

(60) Provisional application No. 61/173,185, filed on Apr. 27, 2009.

(51) Int. Cl.
*G01N 33/53* (2006.01)
*G01N 33/68* (2006.01)
*A01K 67/027* (2006.01)
*C07K 14/78* (2006.01)
*C12N 15/85* (2006.01)

(52) U.S. Cl.
CPC ..... *G01N 33/6887* (2013.01); *A01K 67/0276* (2013.01); *C07K 14/78* (2013.01); *C12N 15/8509* (2013.01); *A01K 2217/075* (2013.01); *A01K 2227/105* (2013.01); *A01K 2267/03* (2013.01); *G01N 2333/78* (2013.01); *G01N 2800/32* (2013.01); *G01N 2800/329* (2013.01)

(58) Field of Classification Search
None
See application file for complete search history.

(56) References Cited

U.S. PATENT DOCUMENTS

| | | |
|---|---|---|
| 6,048,704 A | 4/2000 | Tilson |
| 2004/0126788 A1 | 7/2004 | Schiemann et al. |
| 2004/0157246 A1 | 8/2004 | Shimkets et al. |
| 2005/0282163 A1 | 12/2005 | Epstein |
| 2006/0094054 A1 | 5/2006 | Schiemann et al. |
| 2007/0224643 A1 | 9/2007 | McPherson et al. |
| 2008/0090759 A1 | 4/2008 | Kokenyesi et al. |
| 2010/0317038 A1* | 12/2010 | Granville ........... G01N 33/6893 435/7.92 |

OTHER PUBLICATIONS

Charbonneau et al, JBC, 2003, 278:2740-2749.*
Marshall et al, Circ Res, 2013;113:1159-1168.*
Shinohara et al, Arterioscler Thromb Vasc Biol, 2003; 23:1839-1844.*
Vaughan et al, Circulation, 2001; 103:2469-2475.*
Defawe et al, Cardiovascular Res; 2003; 60:205-213.*
Chiu-Liang Kuo et al. Effects of Fibrillin-1 Degradation on Microfibril Ultrastructure. The journal of Biological Chemistry 2007, Vo. 282 No. 6 pp. 4007-4020 see the whole article.
International Search Report and Written Opinion for PCT/US2010/032551 dated Feb. 22, 2011.

* cited by examiner

*Primary Examiner* — Mark Halvorson
(74) *Attorney, Agent, or Firm* — Baker Botts L.L.P.

(57) ABSTRACT

The present invention makes use of immunoassays, such as sandwich ELISAs, to profile the circulating concentration of elastic fiber and microfibril fragments in samples from individuals with diseases associated with elastic fiber and/or microfibril degradation. Examples of such diseases include, Marfan's syndrome, aortic aneurysm, and scleroderma. Profiling the concentration of such fragments can be used to diagnose disease and monitor disease progression.

10 Claims, 21 Drawing Sheets

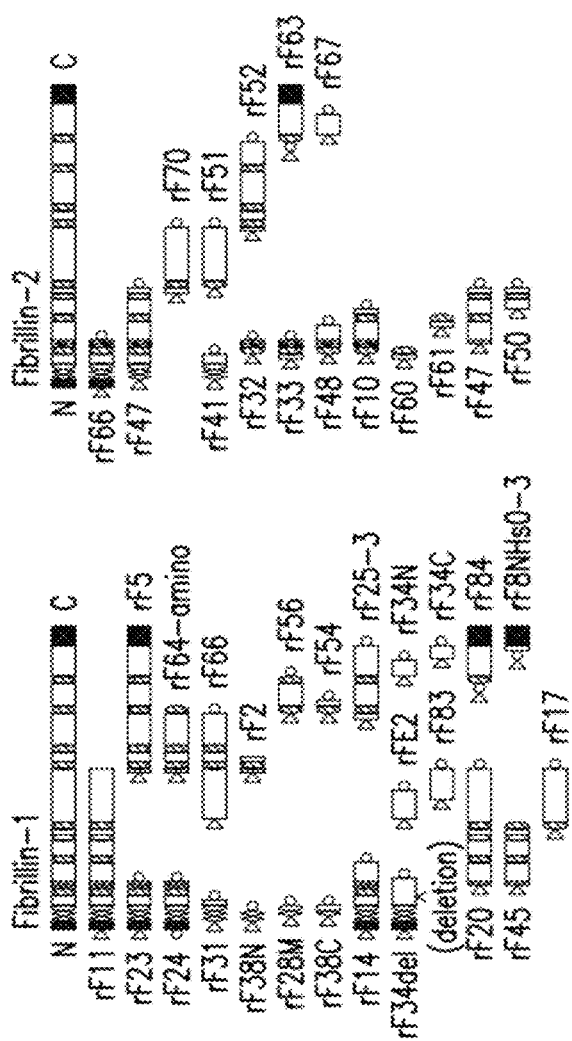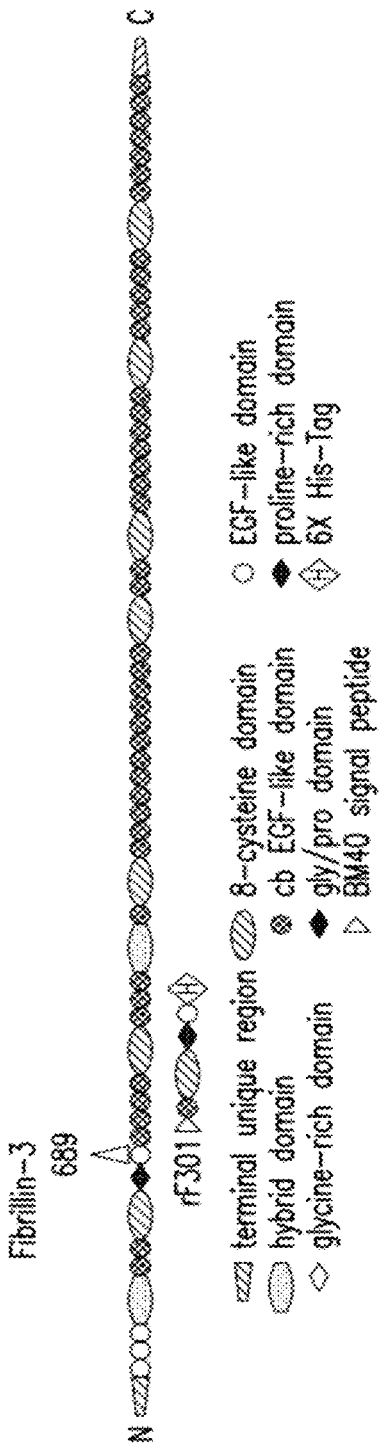
FIG. 7A
FIG. 7B

SEQ ID NO:1 Fibrillin-1: vtdy cqlvryl cqngr ciptpgsyr cec nkgfqldirge ci
SEQ ID NO:2 Fibrillin-2: tidi ckhhanl clngr ciptvssyr cec nmgykqdangd ci
SEQ ID NO:3 Fibrillin-3: tidi crhftnl clngr ciptpssyr cec nvgytqdvrge ci

PROFILING FRAGMENTS OF ELASTIC FIBERS AND MICROFIBRILS AS BIOMARKERS FOR DISEASE

CROSS REFERENCE TO RELATED APPLICATIONS

This application is a continuation of PCT/US2010/032551 filed Apr. 27, 2010, which claims priority to U.S. Provisional Application No. 61/173,185, entitled "Profiling Fragments of Elastic Fibers and Microfibrils as Biomarkers for Disease", filed on Apr. 27, 2009, which are incorporated by reference in their entireties herein.

STATEMENT OF GOVERNMENT INTEREST

This invention was made with government support under grant numbers RO1AR46811 and RC1HL100608 awarded by National Institutes of Health. The government has certain rights in the invention

FIELD OF THE INVENTION

The present invention is directed to methods, compositions, and kits for the detection and monitoring of diseases associated with the degradation of elastic fibers and microfibrils. The methods of the present invention involve measuring the circulating concentration of elastic fiber and/or microfibril fragments as biomarkers for disease. Also disclosed are immunoassays, such as sandwich enzyme-linked immunosorbent assays (ELISA), for the detection and quantification of elastic fiber and/or microfibril fragments, as well as kits, and the compositions contained therein, for performing such assays.

BACKGROUND OF THE INVENTION

Fibrillin-1 (UniProtKB/Swiss-Prot Accession No.: P35555), fibrillin-2 (UniProtKB/Swiss-Prot Accession No. P35556), and fibulin-4 (UniProtKB/Swiss-Prot Accession No. Q9UBX5) are molecular components of elastic fibers and microfibrils. Elastic fibers and microfibrils are stable structures especially abundant in the connective tissues of blood vessels, lung, skin, ligaments and tendons, and the eye. As a result of disease processes, these structures can be degraded by proteases. Examples of diseases that exhibit degradation of elastic fibers and microfibrils are Marfan's syndrome (a heritable disorder of connective tissue affecting 1 in 5,000), cardiac disorders, such as aortic aneurysm and aortic dissection (major health issues in the general population), and scleroderma. As many diseases involving the degradation of elastic fibers and microfibrils present few obvious symptoms, a simple test, such as a blood test, would be highly desirable to increase the rate of early diagnosis and to facilitate monitoring of disease progression. Such a simple test would also facilitate treatment regimens and monitoring of the same.

There are currently no commercially-available assays to measure circulating fragments of elastic fibers and microfibrils. In fact, there are few assays available to measure degradation of connective tissue molecules in general. The assays for osteoporosis that measure bone collagen telopeptide breakdown products are the most successful. However, beyond osteoporosis, the use of connective tissue biomarkers for disease has not been broadly investigated.

Current methods for detecting and monitoring diseases related to degradation of elastic fibers and microfibrils are relatively complex and expensive. For example, in the case of aortic aneurysm, detection methods are limited to analysis of internal anatomy by echocardiogram. In addition, progression of an aortic aneurysm is currently monitored using expensive imaging modalities and is measured by the incremental dilation of the aortic wall. Although such imaging can provide an indication of the growth of an aorta, the costs associated with this technique are substantial. Because of these limited detection and monitoring methods, aneurysms often go undetected until rupture occurs, resulting in severe pain, massive internal hemorrhage, and often death.

To meet the need in the art for simple and relatively inexpensive methods for detecting the degradation of elastic fibers and/or microfibrils, and their associated disease, the present invention relates to methods for detecting and monitoring the circulating concentration of elastic fiber and/or microfibril fragments. In particular, the invention relates to assays (e.g., sandwich ELISAs) that can detect fragments of elastic fiber and microfibril proteins fibrillin-1, fibrillin-2, fibrillin-3, and fibulin-4. The assays of the present invention are useful to identify the degradation of elastic fibers and/or microfibrils, to measure the rate at which degradation (and fragmentation) is proceeding over time, and to determine whether treatments reduce the rate of degradation. The potential value of these assays is significant as diseases associated with degradation of elastic fiber and microfibrils can result in extensive health problems.

SUMMARY OF THE INVENTION

The present invention is directed to methods of profiling the circulating concentration of fragments of fibrillin-1, fibrillin-2, fibrillin-3, and fibulin-4 in samples from individuals with diseases associated with elastic fiber and/or microfibril degradation. Examples of such diseases include, Marfan's syndrome, aortic aneurysm and aortic dissection, and scleroderma. Profiling the concentration of such fragments can be used to diagnose such diseases. Additionally, profiling degradation of elastic fibers and/or microfibrils is useful for monitoring disease progression and response to treatment in such diseases. The invention makes use of immunoassays, such as sandwich ELISAs, and employing antibodies specific for fibrillin-1, fibrillin-2, fibrillin-3, and fibulin-4 for the purposes described herein. The present invention is also directed to kits for performing such immunoassays as well as transgenic animals.

BRIEF DESCRIPTION OF THE DRAWINGS

FIG. 7A-7B: (A) Diagram of banked recombinant fibrillin proteins. These human recombinant proteins are expressed stably in 293 cells and can be purified easily from cell culture medium. (B) Drawing of fibrillin-3 showing domain modules that contain the epitope for monoclonal antibody (mAb689) used in the sandwich ELISAs.

SEQUENCE LISTING

Figure 1A:
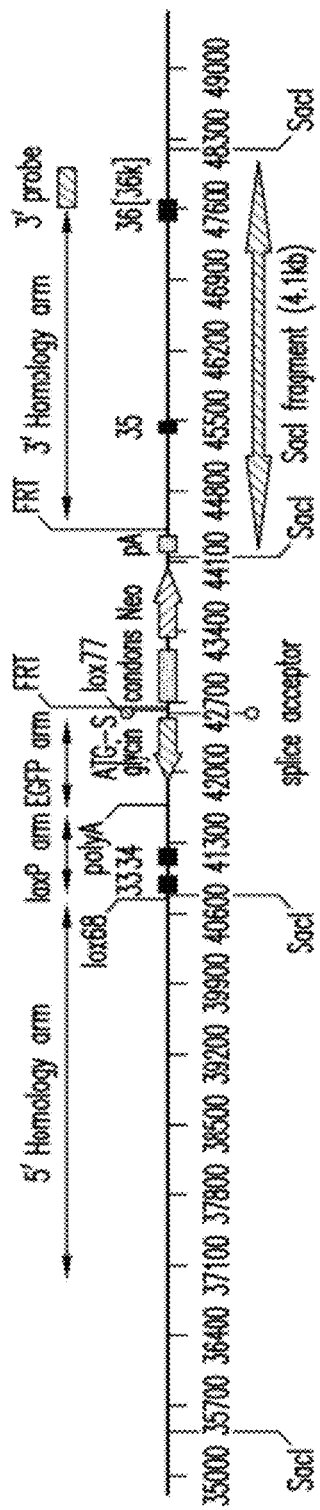
FIGS. 1A-1F. (A) Fbn1 targeted locus contains lox66 and lox77 sites flanking exon 33 and eGFP, in the opposite reading frame. In the presence of Cre-recombinase, these lox sites invert the region between the sites, resulting in the placement of eGFP in-frame after exon 32, truncating the fibrillin-1 molecule after cbEGF17. A line of mice (GT-8) in which inversion and truncation has occurred in all cells were used. (B) Unstained whole-mount confocal microscopy of 2-month GT-8/+ tendon shows incorporation of mutant eGFP-tagged fibrillin-1 into typical, long microfibrils. (C) Unstained 2-month wildtype and GT-8/+ skin sections shows incorporation of mutant eGFP-tagged fibrillin-1 into typical microfibrils in the dermis, in the dermal-epidermal junction, and in the papillary dermis. Scale bar=50 µm. (D) Electron microscopic immunolocalization with gold-conjugated anti-GFP antibodies demonstrates that eGFP-tagged fibrillin-1 is assembled into microfibrils associated with elastic fibers (left panel) and microfibrils without amorphous elastin cores (right panel). Scale bar=500 nm. (E) No differences in the pattern or abundance of fibrillin-1 immunostaining were detected in P3 wildtype and heterozygous GT-8 skin. Anti-fibrillin-1 and anti-GFP immunostainings were also equivalent. Scale bar=50 μm. (F) Neonatal dermal fibroblast cultures were established for all individual pups in a litter, and equal numbers of cells were passaged and plated into wells. Medium was replaced with serum-free medium for 24 hours. Proteins present in the serum-free medium from the individual cultures were TCA precipitated, applied to 5% SDS-PAGE, transferred to nitrocellulose and immunoblotted with anti-fibrillin-1 or with anti-GFP. Fibroblasts from pups 17, 18, 20, and 22 secreted only wildtype fibrillin-1, while fibroblasts from pups 16, 19, and 21 secreted both wildtype and eGFP-tagged and truncated fibrillin-1.

The specification further incorporates by reference the Sequence Listing submitted herewith via EFS on Mar. 15, 2012. Pursuant to 37 C.F.R. §1.52(e)(5), the Sequence Listing text file, identified as 006910_5346SeqList.txt, is 3,716 bytes and was created on Mar. 15, 2012. The Sequence Listing, electronically filed herewith, does not extend beyond the scope of the specification and thus does not contain new matter.

DETAILED DESCRIPTION OF THE INVENTION

The present invention generally relates to a novel method of detecting and monitoring elastic fiber and microfibril diseases in animals and to novel antibodies that selectively bind to elastic fiber and microfibril fragments. More particularly, the present invention relates to the discovery that the presence of specific fiber fragments can be used to predict early disease in animals and that the concentration of such fragments change over time as the disease progresses. Therefore, the methods are useful not only for detection, but also for monitoring disease progression in an animal. Such early detection can assist in proper treatment requirement and can prevent late detection.

The methods of the present invention can be generally accomplished by: (a) obtaining a sample from an animal; and (b) determining the amount of one or more elastic fiber and/or microfibril fragments in the sample. Particular embodiments of the present invention include assays to detect or quantitate elastic fiber and/or microfibril fragments and/or related peptides in a solution (e.g., culture medium, tissue extract and biological fluid); the monoclonal antibodies employed in such assays that bind specifically to individual elastic fiber and/or microfibril fragments; and kits for performing such assays.

Definitions

Unless otherwise defined, all technical and scientific terms used herein have the same meanings as commonly understood by one of ordinary skill in the art to which this invention belongs. Although methods and materials similar or equivalent to those described herein can be used in the practice or testing of the present invention, suitable methods and materials are described below.

It is to be noted that the term "a" entity or "an" entity refers to one or more of that entity. For example, a protein refers to one or more proteins or at least one protein. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, preferably up to +/−10%, more preferably up to +/−5%, and more preferably still up to +/−1% of a given value. Alternatively, particularly with respect to biological systems or processes, the term can mean within an order of magnitude, preferably within 5-fold, and more preferably within 2-fold, of a value. With reference to pharmaceutical compositions, the term "about" refers to a range that is acceptable for quality control standards of a product approved by regulatory authorities.

The term "antibody" is used in the broadest sense, and specifically covers monoclonal antibodies (including full length monoclonal antibodies), polyclonal antibodies, multispecific antibodies (e.g., bispecific antibodies), chimeric antibodies, humanized antibodies, and antibody fragments (e.g., Fab, F(ab')$_2$ and Fv) so long as they exhibit binding activity or affinity for a selected antigen. An antibody that is contemplated for use in the present invention thus can be in any of a variety of forms, including a whole immunoglobulin, an antibody fragment such as Fv, Fab, and similar fragments, a single chain antibody which includes variable domain complementarity determining regions (CDR), and the like. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immuno specific for an antigen or epitope of the invention.

The term "monoclonal antibody" as used herein refers to an antibody obtained from a population of substantially homogeneous antibodies, i.e., the individual antibodies comprising the population are identical except for possible naturally occurring mutations that will be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they can be produced by, e.g., hybridoma culture or recombinantly, uncontaminated by other immunoglobulins. The modifier "monoclonal" indicates the character of the antibody as being obtained from a substantially homogeneous population of antibodies, and is not to be construed as requiring production of the antibody by any particular method.

As used herein, the term "antigen" refers to any substance capable of eliciting an immune response.

"Mammal" refers to any animal classified as a mammal, including human, domestic and farm animals, nonhuman primates, and other animals such as pigs, rodents, rabbits, guinea pigs, hamsters, cows, horses, cats, dogs, sheep, and goats. As used herein, "patient" or "subject" refer to an individual, human, animal, mammal, or cell culture from which a biological sample may be obtained. Such subjects have or potentially have a disease associated with degradation of elastic fiber or microfibrils. Veterinary applications as well as human clinical applications are contemplated by the invention.

As used herein, "detect" refers to the identification of circulating fragments of elastic fibers and/or microfibrils, which are indicative of the existence of a disease condition. As used herein, "diagnose" refers to identification of the existence of a disease. Once a subject is diagnosed with a disease, as used herein, "monitor" refers to following the progression of disease, for example, by obtaining blood samples and testing levels of elastic fiber and/or microfibril fragmentation.

Elastic Fiber and Microfibril Diseases

The methods of the present invention are intended to detect and monitor those diseases associated with degradation of elastic fibers and microfibrils. Elastic fibers are extracellular molecules present in blood vessels in abundant amounts and in cardiac and other connective tissues. Fibrillins assemble into small diameter microfibrils that, together with elastin and other molecules, form the elastic fibers that impart elasticity to tissues. In addition to being abundant in blood vessels, fibrillin and microfibrils are present in cardiac muscle and valve tissue where thin sheets of connective tissue, largely basement membrane and fibrillin, surround each muscle fiber.

In a diseased state, degradation of elastic fibers and microfibrils results in the release of elastic fiber and/or microfibril fragments. Disorders that result in degradation of microfibrils can result in degradation of other fibrillin and fibulin types in particular profiles. Without being bound by theory, and because, in contrast to typical elastic fibers in the dermis and perichondrium, microfibrils are not easily visualized by electron microscopy, degradation studies, such as those outlined in Example 1, provide indications as to how such profiles are established. For example, Example 1 provides evidence that fibrillin-1 is present on the outside of microfibrils, and thus is considered the initial target for protease-mediated fragmentation. In contrast to the externally arranged fibrillin-1 proteins, fibrillin-2 and also fibulins 3, 4, and 5 are localized on the inside of fibrillin microfibrils and thus are considered markers of extensive degradation of the fibers. Accordingly, the circulating concentrations of fragments of particular proteins will correlate to early stages of elastic fiber disease or mild disease, while other concentrations of other fragments correlate with more severe or advanced disease.

In the present invention, the circulating concentration of such fragments is profiled to detect, diagnose, and/or monitor disease. Examples of diseases that can be diagnosed and monitored by the present invention include, but are not limited to, scleroderma, cardiovascular diseases such as aortic aneurysm and aortic dissection, and Marfan's syndrome. In each of these diseases, elastic fibers and microfibrils are degraded, leading to a change in the amount of elastic fiber and/or microfibril fragments circulating in the blood stream. As discussed in detail below, specific fragment profiles have been correlated to specific disease states.

The methods described here are useful in diagnosing and monitoring progression of scleroderma in subjects. Scleroderma is a chronic connective tissue disease. Individuals with this disease have general fatigue, joint or bone aching, stiffness of hands and feet, skin discoloration, swallowing difficulties, skin thickening and tightness, dry mucus membranes, calcium deposits under the skin or Raynaud's phenomenon. Individuals with scleroderma can also have inflammation and fibrosis of blood vessels. This fibrosis is associated with the release of fibrillin-1 fragments. Accordingly, assaying the circulating concentration of elastic fiber fragments, including but not limited to fibrillin-1 fragments, allows for diagnosis and monitoring of scleroderma.

The methods described herein are also useful in diagnosing and monitoring cardiovascular disorders. Fibrillin-1 is an important and abundant component of cardiovascular tissues, and, as such, the circulating concentration of Fibrillin-1 fragments can be a useful marker for identifying cardiovascular disorders including aneurysm, aortic aneurysm, aortic dissection, atherosclerosis, cardiac or pulmonary fibrosis, cardiac hypertrophy, cerebrovascular disease, congestive heart failure, coronary artery disease, heart attack, heart valve disease, peripheral vascular disease, or stroke.

In one specific embodiment of the invention, patients are screened for aortic aneurysms. Aortic aneurysms are generally defined as swelling of the aorta and can appear in different locations throughout the body. Examples of types of aneurysms include aortic root aneurysm, thoracic aortic aneurysm, abdominal aortic aneurysm, and thoracoabdominal aortic aneurysms. As the aorta swells, a defect in the protein construction of the aortic wall occurs as the fibers are stretched and fragment. In patients with aortic aneurysms, the levels of fibrillin-2 and fibulin-4 fragments increase as fibrillin-1 fragments levels decrease in the blood. Accordingly, assaying the circulating concentration of elastic fiber fragments, including but not limited to fibrillin-1, fibrillin-2, and fibulin-4 fragments, allows for diagnosis and monitoring of aortic aneurysms.

The methods described herein are useful to diagnose, prognose, or monitor progression of subjects with Marfan's syndrome, a genetic disorder of the connective tissue, that is attributable to point mutations in the gene that encodes the connective protein fibrillin-1. Marfan's syndrome can lead to aortic aneurysm, aortic or mitral valve regurgitation, mitral valve prolapse, or congestive heart failure. In patients with Marfan's syndrome, fibrillin-2 fragments circulating in the blood increase as fibrillin-1 fragment levels decrease as the disease progresses. Accordingly, assaying the circulating concentration of elastic fiber fragments, including but not limited to fibrillin-1 and fibrillin-2 fragments, allows for diagnosis and monitoring of Marfan's syndrome.

In addition to diagnosis and monitoring of diseases related to the degradation of elastic fibers, the present invention also finds use in treatment regimens and in monitoring treatment regiments for such diseases. In particular, the present invention may be used in the course of a particular treatment as a routine test for monitoring progression, or to obtain an indication that additional and/or alternative treatment is warranted. In addition to routine use of the instant invention as part of an on-going treatment, the instant invention can be used to monitor therapies and/or other treatment modalities (e.g., surgical interventions, antibiotic prophylaxis, and administration of beta-blockers).

Sample Collection

As noted above, the methods of the present invention can be used to diagnose and detect disease through analysis of biological samples of bodily fluids. Biological samples refer to any fluid obtainable from a subject, the constituents of which can be analyzed using immunological techniques. The biological sample can be, for example, blood, serum, plasma, urine, saliva, sputum, mucus, semen, amniotic fluid, mouth wash and/or bronchial lavage fluid, in which soluble elastic fiber-associated proteins or fragments thereof are found. A sample for analysis can be obtained from a subject using methods known to those of skill in the art. For example, such samples can be taken, and analysis conducted, in the context of an annual physical.

The methods described herein can also be used to analyze biological samples obtained from cell culture. Typically, cells that secrete an elastic fiber-associated protein can be maintained in a suitable medium using routine culturing methods for a period of time suitable for secretion of the protein. The medium containing the protein can be separated from the cells for example by decanting, centrifugation, or filtration. An elastic fiber-associated protein present in cell culture medium may be subjected to protease activity, which can then be detected and measured.

Once patients are diagnosed or disease is detected, patients can be monitored for disease progression. Through simple blood tests, changes in fragmentation profile (which reflect disease progression) can be measured. With easier patient compliance in testing, the need for specific treatments or surgical intervention will be easier to predict, determine, and follow.

Immunoassays

In the present invention, various means for profiling the circulating concentration of elastic fiber fragments can be used, including, but not limited to immunoassays, and mass spectrum analysis. In certain embodiments, immunoassays are used to detect the presence of elastic fiber and microfibril fragmentation. Such immunoassays include but are not limited to sandwich ELISAs, inhibition ELISAs, radioimmunoassays, florescence immunoassays, and chemiluminescent immunoassays. In a specific embodiment of the present invention, a sandwich ELISA is used.

In one embodiment of the present invention, the sandwich ELISA is used to profile the circulating concentration of elastic fiber fragments in the sample blood serum. Generally speaking, in the sandwich ELISA, a surface is first prepared to which a known quantity of capture antibody is bound. Any nonspecific binding sites on the prepared surface are blocked. Then, an antigen-containing sample is added to the surface, and the surface is washed to remove unbound antigen. In certain embodiments, a second unlabeled antibody capable of binding the antigen is then added. In such embodiments, a third, enzyme-linked, antibody that is specific to the constant region of the second antibody can be then added. The surface is then washed so that unbound antibody-enzyme conjugates are washed away. A chemical is then added to trigger a signal, e.g., a color, or electrochemical signal that can be measured. The signal is then measured to determine the presence and quantity of target fragments. In alternative embodiments the second antibody is itself labeled or linked to an enzyme, thereby mooting the need for a third antibody.

Surface

The solid phase used as the surface on which the immunoasssay will be performed may be any inert support or carrier that is essentially water insoluble, including supports/carriers in the form of surfaces, particles, pourous matrices or the like. Exemplary supports/carriers include small sheets, Sephadex™, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogen bromide-activated carbohydrates and reactive substrates can be suitably employed for capture reagent immobilization.

In one embodiment, the immobilized capture reagent is coated on a microtiter plate, and in particular the solid phase is a multi-well microtiter plate that can be used to analyze several samples at one time. Examples of microtiter plates include 96-well Elisa plates, such as Maxisorb™ or Immulon™ (Nunc, Roskilde, Denmark). Additionally, multiplex ELISA technologies, such as the Luminex™ technology may be employed to run hundreds of ELISAs simultaneously (Millipore). Such multiplex ELISA assay techniques are well known in the art and include, in addition to the Luminex™ technology, a variety of technologies that involve the use of multiple capture and/or detection antibodies for interrogating numerous analytes simultaneously. Discrimination among the various detection antibodies in such multiplex assays involves the use of multiple, distinct labels. Alternative multiplex assays technologies include the LiquiChip™ system (Qiagen) and the BD™ Cytometric Bead Array (BD Bioscience).

Capture Antibodies

The use of monoclonal antibodies against elastic fiber and microfibril fragments to establish the elastic fiber and microfibril fragment profiles of histological, cytological and biological fluid samples is an advantageous approach to disease diagnosis and therapy monitoring. Because of the high specificity and sensitivity of monoclonal antibodies, early detection of certain fiber-related pathological conditions is possible as is early assessment of the efficacy of certain therapeutic programs. Monoclonal antibodies are ideal for employment in quantitative assays because they are epitope specific and can detect minor structural differences between individual types of elastic fiber and microfibril fragments.

As disclosed below, hybridoma cell lines can be generated to produce monoclonal antibodies reactive with elastic fiber and/or microfibril fragments. Antibodies produced by such hybridomas can be employed in the profiling of elastic fiber and microfibril fragments. The immunoassays described below, which take advantage of the high specificity and affinity of such monoclonal antibodies, can be utilized for the measurement of elastic fiber and microfibril fragments found in body fluids.

The hybridoma cell lines of the present invention can be produced by various methods generally known to those of ordinary skill in the art. In general, the method involves immunizing suitable mammals (for example, mice) with the antigens of interest, fusing antibody producing cells isolated from the spleen of the animal with myeloma cells, cloning the resulting hybrid cells and selecting those cells which produce the desired monoclonal antibody that binds the antigen of interest.

Immunizations are usually performed with purified antigens. The usual mammals used for immunizations are mice, but other mammals and various mouse strains can also be employed. The immunizations are performed in a manner known in the art, such as by administering intraperitoneally, intravenously and/or subcutaneously three to six injections each containing an appropriate amount of purified antigen (i.e., from about 1 microgram to about 200 micrograms) at intervals of about one to six weeks, usually together with an adjuvant that stimulates the production of lymphocytes, e.g., complete or incomplete Freund's adjuvant. Antibody-producing cells present in the spleen of the immunized animals are taken from the animals two to six days after the last ("booster") immunization and fused with myeloma cells of a suitable cell line. Myeloma cell lines and cell lines derived therefrom are known as suitable fusion partners. The myeloma cell line is generally derived from the same species as the immunized mammal, since intra-species hybrids are more viable than inter-species hybrids. Suitable culture media for the growth of the hybrid cells are the customary standard culture media, for example, RPMI Medium or medium containing 20% fetal calf serum which is supplemented with antibodies. At the beginning of cell growth, so-called feeder cells (e.g., normal mouse peritoneal exudate cells, spleen cells, bone marrow macrophages or the like) can be added. Advantageously, the cell supernatants are tested in an immunoassay, for example, an enzyme immunoassay, that demonstrates the binding of monoclonal antibodies to the antigen of interest. Those hybridomas that produce antibodies having the desired specificity as well as other desirable characteristics can then be maintained as viable cultures and/or frozen for storage.

The present invention encompasses all monoclonal antibodies exhibiting the characteristics of the antibodies described herein. In other words, antibodies having the patterns of reactivity illustrated herein are within the scope of the invention regardless of the immune globulin class or subclass to which they belong. For example, a suitable monoclonal antibody can be of class IgG1, IgG2a, IgG2b, IgG3, or of classes IgM, IgA, or of other known Ig classes.

The selected capture antibodies of the present invention are immobilized on a suitable substrate by any method available to one of skill in the art. The antibody can be linked directly to a selected functional group on the substrate. Alternatively, the antibody can be linked indirectly to the substrate via a linker or spacer. In certain non-limiting embodiments, linkage can be achieved by covalently attaching the capture antibody to streptavidin (or biotin) and then attachment to the substrate occurs indirectly via a biotin (or streptavidin) moiety that is covalently linked to the substrate. Alternatively, a thiol-terminal silane can be used for coating of the substrate surface, and a heterobifunctional crosslinker, e.g., N-gamma-maleimidobutyryloxy succinimide ester (GMBS). can be used for antibody attachment. See U.S. Pat. No. 5,077,210. With this method, the antibody can be immobilized at a high density (e.g., 2 ng/mm$^2$).

Another type of surface immobilization technique uses polymer hydrogel matrices. These materials typically contain a large amount of water, are soft, and are bioinert. Examples include cross-linked polymer films of poly(vinyl alcohol) and films of carboxymethyldextran. See Kobayashi, J. and Y. Ikada, "Covalent Immobilization of Proteins Onto the Surface of Poly(vinyl alcohol) Hydrogel," Biomaterials, 12, (1991), pages 747-751; Johnsson, B. et al, "Immobilization of Proteins to a Carboxymethyldextran-Modified Gold Surface for Bio specific Interaction Analysis in Surface Plasmon Resonance Sensors," Anal. Biochem., 196, (1991), 268-277; Lofas, S. and B. Johnsson, "A Novel Hydrogel Matrix on Gold Surfaces in Surface Plasmon Resonance Sensors for Fast and Efficient Covalent Immobilization of Ligands," J. Chem. Soc. Commun., (1990), pages 1526-1528.).

Capture antibodies of the present invention include, but are not limited to the following. Fibrillin-1 monoclonal antibodies include, but are not limited to mAb 15, 26, 56, 60, 61, 68, 69, 78, 90, 120, 201, and F2-32. The epitopes bound by these exemplary anti-Fibrillin-1 antibodies are (mAb: epitope residues in full-length sequence): mAb15: 417-436; mAb 26: 330-401; mAb 56: 2068-2389; mAb 60: 2068-2389; mAb 61: 2068-2389; mAb 68: 2068-2389; mAb 69: 2068-2389; mAb 78: 288-329; mAb 90: 2068-2389; mAb 120: 2068-2389; mAb 201: 613-722; and mAb F2-3: 2068-2389. Fibrillin-2 monoclonal antibodies include, but are not limited to mAb 48, 143, 60, 72, and 205. Fibrillin-3 monoclonal antibodies include, but are not limited to, mAb 129, 317, 405, 471, 511, and 689. Fibulin-4 monoclonal antibodies include, but are not limited to, mAb 56, 156, 204, 226, 347, 492, and 597.

In addition, the function provided by the capture antibody, e.g., binding particular elastic fiber fragments to the substrate surface, can be accomplished using alternatives to traditional monoclonal antibodies. Alternatives to traditional monoclonal antibodies include antibody mimetics, such as, but not limited to, affibodies, domain antibodies, nanobodies and unibodies as well as the binding domains of other proteins, such as elastic fiber binding proteins.

Fragments

In the present invention, various fiber fragments are interrogated. These include, but are not limited to fibrillin and fibulin fiber fragments, such as, but not limited to, fragments of fibrillin-1, fibrillin-2, and fibulin-4. In particular, exemplary fragments of fibrillin-1 include, but are not limited to fragments containing the following residues of the full length fibrillin-1 protein: 417-436 330-401, 2068-2389, 288-329, and 613-722.

Various levels of elastic fiber fragments in the blood stream can be indicative of specific disease states. For example, in patients with aortic aneurysms, the levels of fibrillin-2 and fibulin-4 fragments increase as fibrillin-1 fragment levels decrease in the blood. In patients with Marfan's syndrome, fibrillin-2 fragments increase as fibrillin-1 fragment levels decrease in the blood. Accordingly, profiling the circulating concentration of elastic fiber fragments, including but not limited to fibrillin-1, fibrillin-2, fibrillin-3, and fibulin-4 fragments, allows for diagnosis and monitoring of certain diseases.

Figure 5A:
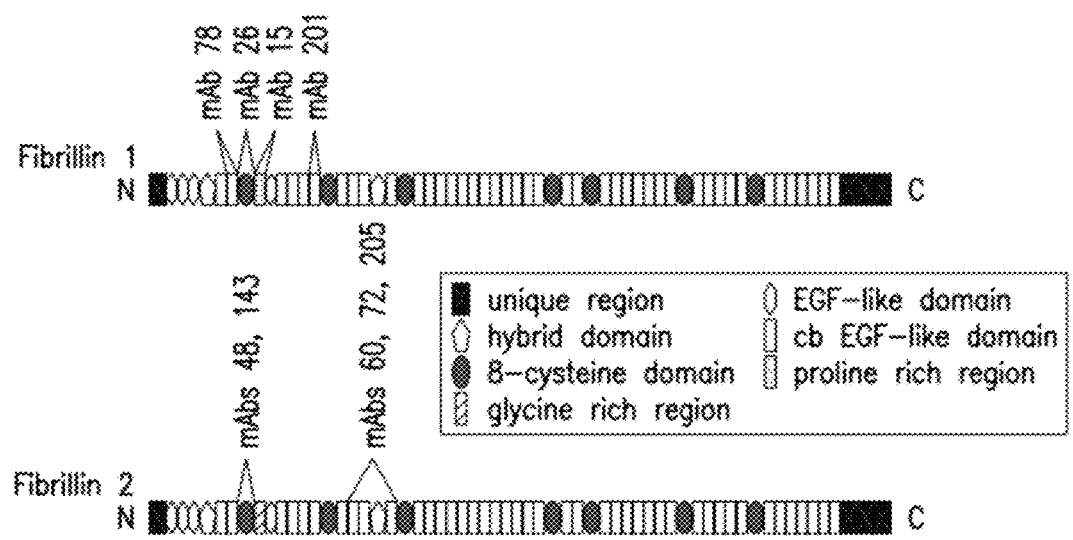
FIGS. 5A-5B. (A) Drawings of fibrillin-1 and fibrillin-2 show domain modules that contain the epitopes for monoclonal antibodies used in the sandwich ELISAs. (B) Scatter plots demonstrated statistically significant profiles of circulating fragments of fibrillin-1 and fibrillin-2 in Marfan's syndrome and scleroderma, compared to control samples. Samples were not separated by age, gender, or severity of disease. Capture/detector antibody pairs identified different informative fragments in Marfan's syndrome samples compared to scleroderma samples. Table 1 shows results for all antibody pairs tested.

In the course of disease progression, the elastic fibers may be degraded to produce different fragments. Profiling of these distinct fragments is accomplished by employing antibodies specific to particular epitopes on the full length protein. For example, and not by way of limitation, FIG. 5A depicts the various locations specific antibodies bind to Fibrillin-1 and Fibrillin-2 and FIG. 7B depicts the location a specific antibody binds to Fibrillin-3. In the case of Fibulin-4, the monoclonal antibodies identified above have been found to bind epitopes on the N-terminal half of the protein.

Detection Antibody

After immobilization of a selected capture antibody onto a suitable substrate, and exposure of that capture antibody to a sample for profiling, it is necessary to visualize binding of the elastic fiber fragment to the capture antibody. Such visualization is commonly accomplished via the addition of a detection antibody that specifically binds an epitope on the elastic fiber fragment bound by the capture antibody.

The detection antibodies may be detected directly through moieties such as fluorochrome, chemiluminescent, and radioactive labels, or indirectly through moieties, such as enzymes, that must be reacted or derivatized. Examples of moieties that can be detected directly include radioisotopes, fluorophores such as rare earth chelates or fluorescein and its derivatives; rhodamine and its derivatives. Examples of moieties that must be reacted or derivatized include, but are not limited to dansyl; umbelliferone; luciferases; luciferin, 2,3-dihydrophthalazinediones; horseradish peroxidase; alkaline phosphatase; b-galactosidase; glucoamylase; lysozyme; saccharide oxidases; heterocyclic oxidases; biotin/avidin; biotin/streptavidin; biotin/streptavidin-HRP; spin labels; baceriophage labels; stable free radicals; and the like. Conventional methods are available to bind these detectable moieties covalently to a detection antibody. For example, coupling agents such as dialdehydes, carbodiimides, dimaleimides, bis-imidates, bis-diazotized benxidine, and the like may be used to tag the antibodies with the above-described labels.

Because the two antibodies in a sandwich assay operate most effectively when they each bind the target antigen but do not interact or bind to each other, the immobilized capture antibody is tested for reactivity with the detection antibody, or in the case of a three antibody system, the secondary and detection antibodies. A low reactivity is preferred between the capture antibody and the detection antibody while retaining high affinity for the target antigen. Furthermore, antibody pairs will operate most effectively when they each bind the target antigen at distinct locations. Accordingly, antibodies should be evaluated to avoid pairing those with overlapping binding specificities.

One aspect of certain assays described herein is the selection of appropriate antibody pairs for performing the assay. Skilled artisans will recognize that antibody pairs can be selected that bind in combination to a fragment of an elastic fiber-associated protein. For example, to detect an amino-terminal fragment of a specific fibrillin, antibodies can be chosen near the ends of the predicted fragment. For example, the antibody pair mAB 15/mAb 201, together can bind a fragment comprising the amino-terminal half of fibrillin-1, whereas the antibody pair mAb 15/mAb 69 does not. Accordingly, since different disorders yield different fragments, specific antibody pairs can be chosen to detect profiles relevant to specific diseases.

For example, and not by way of limitation, antibody pairs mAb 78/mAb 26, mAb 78/mAb 201, mAb 15/mAb 26, mAb 78/mAb 201, and mAb 72/mAb 143 can be used to detect fibrillin-1 fragments in Marfan's syndrome subjects. Antibody pair mAb 48/mAb 60 can detect fragments associated with aortic aneurysm. Antibody pairs mAb 15/mAb 201, mAb 15/mAb b26 and mAb 78/mAb b26, and mAb 78/mAb b201 and mAb 15/mAb b201 can detect fibrillin-1 fragments in patients with scleroderma. These antibody pairs are only examples of how circulating fragments can be interrogated and correlated for use in diagnosis or therapy.

Transgenic Animals

In certain embodiments the present invention relates to transgenic animals. In such embodiments, an animal of the present invention can be a transgenic animal with a genome alteration. For example, but not by way of limitation, a transgenic animal of the present invention can be capable of expressing one or more recombinantly-derived polypeptides. In certain embodiments the transgenic animal has been modified to be deficient, either heterozygous or homozygous, in expression of one or more polypeptides ("gene-deficient"). Such capability for expression or deficiency in expression can be conditional. In specific embodiments the recombinant peptide expressed by the transgenic animal is a fibrillin or fibulin protein. In certain embodiments, the polypeptide is fibrillin-1, fibrillin-2, fibrillin-3, and fibulin-4. In certain embodiments the recombinantly-derived polypeptide is a mutant form of fibrillin or fibulin-4. In certain embodiments the recombinantly-derived polypeptide is linked to a marker, such as, but not limited to a fluorescent marker such as, but not limited to eGFP. Alternative markers, including alternative fluorescent markers are well known in the art.

A transgenic animal of the present invention can be prepared by a method known in the art. For example, a transgenic animal of the present invention can be prepared by introducing a polynucleotide encoding a polypeptide of interest, such as fibrillin-1, fibrillin-2, fibrillin-3, or fibulin-4, operatively to a specified promoter (e.g., in the form of an expression vector) into a fertilized egg of an animal or another cell (e.g., unfertilized egg, spermatozoon or a progenitor cell thereof) in the initial stage of development. Examples of methods of gene introduction include, but are not limited to, electroporation, lipofection, calcium phosphate co-precipitation, and microinjection. A transgenic animal of the present invention can be an animal prepared by mating a thus-prepared animal and another animal of the same species.

A gene-deficient animal of the present invention can be prepared by a method known in the art. For example, a gene-deficient animal of the present invention can be prepared using an embryonic stem cell (ES cell) specifically lacking a particular gene or portion of a gene, including but not limited to one or more genes coding for fibrillin-1, fibrillin-2, fibrillin-3, and fibulin-4. An ES cell can be prepared by, for example, introducing a specified targeting vector into ES cells, and selecting an ES cell showing homologous recombination from among the ES cells incorporating the targeting vector.

In certain embodiments, a targeting vector capable of inducing homologous recombination that causes specific expressional failure of a polynucleotide or polypeptide of the present invention can be used. In certain embodiments, such a targeting vector comprises a first polynucleotide and second polynucleotide that are homologous or specifically homologous to a gene of interest (such as a gene encoding fibrillin-1, fibrillin-2, fibrillin-3, or fibulin-4) and, as required, a selection marker. The first and second polynucleotides are polynucleotides having a sequence identity and length that are sufficient to produce homologous recombination in the genomic DNA associated with the gene of interest. The first and second polynucleotides are chosen in a way such that specific deficiency of a particular isoform is produced. In certain embodiments, positive selection markers (e.g., neomycin resistance gene, hygromycin B phosphotransferase (BPH) gene, blasticidin S deaminase gene, puromycin resistance gene), negative selection markers (e.g., herpes simplex virus (HSV) thymidine kinase (tk) gene, diphtheria toxin A fragment (DTA) gene) and the like can be employed. In certain embodiments the targeting vector can comprise either a positive selection marker or a negative selection marker or both. Furthermore, the targeting vector can comprise two or more recombinase target sequences (e.g., loxP sequence, which is used in the Cre/loxP system derived from bacteriophage P1, FRT sequence, which is used in yeast-derived FLP/FRT system).

A gene-deficient animal of the present invention can be prepared by transplanting into an animal a chimeric embryo obtained by introducing an ES cell obtained as described above into an embryo, and then mating the chimeric animal obtained. As examples of the embryo, blastocysts, 8-cell stage embryos and the like can be mentioned. The embryo can be obtained by mating a female animal undergoing an overovulation treatment with a hormone preparation (for example, PMSG, which has FSH-like action, and hCG, which has LH action, are used) and the like with a male animal, and the like. Exemplary methods of introducing an ES cell into an embryo include, but are not limited to, the micromanipulation method, the aggregation method and the like.

In certain embodiments, the animal receiving a chimeric embryo transplanted is preferably a pseudo-pregnant animal. A pseudo-pregnant animal can be obtained, for example, by mating a female animal in the normal sexual cycle with a male animal emasculated by vasoligation. The animal incorporating the chimeric embryo becomes pregnant and delivers a chimeric animal. Whether or not the animal born is a chimeric animal can be determined by a method known in the art, for example, by the body color or coat color. For the determination, a DNA may be extracted from a portion of the body and subjected to Southern blot analysis or PCR assay.

An animal of the present invention can be useful in, for example, developing a pharmaceutical (e.g., a prophylactic or therapeutic drug as described above), reagent or food, identifying a further marker gene specific for disease, and analyzing mechanisms associated with disease. For example, but not by way of limitation, expression profile analysis can be performed comprising measuring an expression profile (particularly expression profile of a disease cell or tissue) using a microarray, protein chip (e.g., antibody chip, or non-antibody chip) and the like in an animal of the present invention, and comparing the profile with the expression profile of a control animal. An animal of the present invention can also be useful as an animal model of disease.

Statistical Analysis

As fibrillin assays are being conducted, quality control procedures can be employed to facilitate the gathering of high quality, reproducible data. In certain embodiments, these procedures involve 'real-time' analysis to monitor quality and to evaluate the stability of the assay procedures. In non-limiting, exemplary, embodiments, such analyses focus on the use of standard curves. In such embodiments, the equation representing the curve can be derived from an appropriate method, such as, but not limited to, the four-parameter model. This model allows the entire range of the control values to be used. The fitted curve is then used to back-calculate absorbance level and to compute the percent recovery, which is plotted and inspected. In certain embodiments another set of analyses focus on the precision of the replicates produced in the assay. In such embodiments, replicates of standard controls and of the patient samples can be evaluated. The coefficient of variation is typically used and expressed as a percent (CV %). The CV % for each unique set of replicates is computed and plotted against the average value of the replicates. The resulting graph enables a clear visualization of replicates with substantial variability and facilitates decisions about repeating the assay or eliminating values based on pre-specified criteria (e.g., CV %>20%). In situations where duplicate measures are produced (as compared to triplicates), the difference between the duplicates can be plotted against the mean of the duplicates using the Bland-Altman method. Observations outside the limits-of-agreement can be clearly visualized using such methods, which can facilitate decisions about repeating the assay or eliminating the observation, and such decisions can be made in accordance with pre-determined standardized procedures. Plotting replicate CV % s against the mean or using the Bland-Altman approach as data accumulate is useful for ongoing monitoring of the assay. In certain embodiments, issues arising from drift in technique or reagents become apparent in these plots. Such on-going monitoring preserves the volume of biologic samples obtained in clinical and epidemiologic studies, which can limit specimen collection to reduce participant burden.

The fibrillin assays of the instant invention produce a considerable amount of data that needs to be managed and summarized for analysis. In certain embodiments, absorbances and concentrations are produced for 4 or more fragments for fibrillin-1, 3 or more fragments for fibrillin-2, and can include data relating to the overall concentration of fibulin 4. In such embodiments, this results in at least 8 unique variables. Given this large volume of data, several analytic approaches are possible and the use of any one approach, or combinations of approaches, will be determined by the specific characteristics of the data being gathered and the particular embodiment of the invention.

The first, non-limiting, exemplary approach involves the evaluation of individual fragment data. In these analyses, the raw absorbance (or concentration) values will be used. In certain embodiments the first step in the analysis is to graphically represent the distribution of the fragment levels in order to determine the shape of their distribution. For fragments that are approximately normally distributed, fragment levels can be categorized into groups, such as, but not limited to quintiles or quartiles, depending on the number of patients in the sample. Categorization of the fragment levels in this way minimizes the possibility that extreme observations will have undue influence in subsequent analyses. For fragments that have a narrow distribution or for those with a large proportion of undetectable levels, the fragment can be categorized as either present or absent. In the next step, the fragments can be cross-classified using contingency tables. In certain embodiments, chi-square tests can be used to examine the association of fragment levels within the molecule (e.g., but not by way of limitation, between four distinct fibrillin-1 fragment levels) and between molecules (e.g, but no by way of limitation, between fibrillin-1 and fibrillin-2 fragment levels). In certain embodiments, a third step can be used that involves further descriptive analyses to discern associations of the fragment levels with demographic or other characteristics of the patient sample. In certain embodiments, this step can make use of appropriate regression models to address the study hypotheses. For example, but not by way of limitation, if the hypotheses posed pertain to the association of fibrillin fragments with clinical or other outcomes, the fibrillin variables can be fit into the appropriate regression model as dependent variables. In contrast, if the hypotheses pertain to effects of other measures on variability in fibrillin levels, then appropriate models can be chosen in order to fit the fibrillin measure as the dependent variable. For example, if the absorbance or concentration of a particular fragment is approximately normally distributed, the variable representing that fragment can be fit as the dependent variable in generalized linear regression models. If the fragment level is categorized, an appropriate method for a dichotomous dependent variable (e.g., logistic regression or log-binomial regression) or categorical dependent variable (e.g., polytomous logistic regression) can be used.

In certain embodiments, a second approach can be used that involves clustering procedures. In such embodiments, classification of fibrillin fragment absorbances (or concentrations) into unique groupings ('clusters') can be accomplished with the k-means clustering procedure. This procedure is available in most statistical software packages. The k-means procedure uses values called Euclidean distance to place individuals from the entire study sample into mutually exclusive groups that maximize between-group variation and minimize with-in group variation. The advantage of k-means clustering is that it does not depend on the user to decide a specific number of clusters to be used. Several steps are traditionally used to determine the appropriate number of clusters. Once the appropriate number of clusters is identified given the data, the distributions of the fragment concentrations in each cluster can be evaluated. In certain embodiments clusters generally representing different combinations of higher and lower fibrillin-1 and fibrillin-2 fragment concentrations can become apparent. For example, but not by way of limitation, one cluster likely will be characterized by low values of all fibrillin fragments. The final cluster variables can be used as either independent or dependent variables in regression models for subsequent statistical analyses.

Kits

The invention provides kits that comprise at least a first capture antibody immobilized on a solid substrate, for example, and not by way of limitation, the well of a microtiter plate or a bead, and at least a first detection antibody. In one embodiment, the invention provides kits comprising a solid substrate with an immobilized capture antibody, a container with a detection antibody preparation and instructions for using such a substrate to detect a target antigen that selectively binds to the immobilized capture antibody and the detection antibody preparation. The kit can also contain a container with a negative control sample (e.g. components frequently encountered in samples that contain the target antigen); a container with a positive control sample (e.g., the target antigen); and/or a container with sample diluent.

To use the kit of the present invention, a sample is diluted in sample diluent (if necessary), and then placed in contact with the capture antibody (e.g., immobilized on a solid substrate, such as a well of a 96-well microtiter plate) and the detection antibody preparation for a time and under conditions for any target antigen present in the body fluid to bind to the capture antibody and the detection antibody preparation. The binding is then detected via a label attached to the detection antibody.

EXAMPLES

The present invention will be better understood by reference to the following Examples, which are provided as exemplary of the invention, and not by way of limitation.

Example 1: Microfibril Fragmentation in Marfan's Syndrome

Mutant fibrillin-1 initiates disease-causing changes in the extracellular matrix either by interfering with the assembly of microfibrils (Dietz et al., Genomics. 1993 August; 17(2):468-75; Eldadah et al., J Clin Invest. 1995 February; 95(2):874-80), by destabilizing microfibrils (Reinhardt et al., (1997) J. Biol. Chem. 272, 1231-1236; Reinhardt et al., (2000) J. Biol. Chem. 275, 12339-12345), by fibrillin-1 deficiency (Pereira et al., Proc Natl Acad Sci USA. 1999 Mar. 30; 96(7):3819-23) or haploinsufficiency (Judge et al., J Clin Invest. 2004 July; 114(2):172-81), or by activating TGF signaling (Neptune et al., Nat Genet. 2003 March; 33(3):407-11; Habashi et al., Science. 2006 Apr. 7; 312 (5770):117-21). Because fibrillin-1 is a large molecule and most mutations cause single amino acid differences or small deletions, it has been impossible to distinguish mutant from wildtype fibrillin-1 and to determine how mutant fibrillin-1 affects microfibril assemblies. Previous cell culture studies have used total fibrillin-1 synthesis and deposition into the extracellular matrix as readouts for the effects of mutant fibrillin-1 (Brenn et al., Lab Invest. 1996 September; 75(3):389-402; Eldadah et al., J Clin Invest 1995 February; 95(2):874-80; Aoyama et al., J Clin Invest 1994 July; 94(1):130-7.

Example 1.1 Production of GT-8 Mouse

To gain insight into the effects of mutations in fibrillin-1 on the assembly and stability of microfibrils, mice in which mutant fibrillin-1 is truncated and tagged with eGFP were generated. Currently there are no mice in which extracellular matrix ("ECM") proteins are tagged with GFP by homologous recombination, because ECM proteins are somewhat difficult to tag and because tagging ECM proteins can perturb the function of these proteins. Tagging a truncated form of fibrillin-1 is the first time this technology has been used successfully for an ECM protein. It has been useful because it allows us, for the first time, to ascertain the presence of the mutant fibrillin-1 in extracellular microfibrils. In addition, the mutant mouse is a good in vivo model for Marfan syndrome and aortic disease. This mouse model of Marfan syndrome will allow us to test for elastic fiber fragments in the blood of these mice, in order to determine whether the profile and/or abundance of the fragments reflect aortic disease progression. In addition, because these mice were generated to harbor a "conditional" mutation, the tagged fibrillin-1 can be produced only by the smooth muscle media of blood vessels, and can therefore determine whether or not fragments in the blood are coming specifically from blood vessels.

In addition to these aspects, the new mouse model is generally useful as an in vivo "reporter" mouse for fibrillin-1 production. No such in vivo model currently exists. Such a "reporter" mouse can be used as an experimental animal to test compounds (for example, compounds for cosmetics as well as therapeutic compounds) that can be used to increase the production of fibrillin-1. Since fibrillin-1 is a major functional component of all connective tissues, increasing the amounts of fibrillin-1 produced by cells in an in vivo model has a variety of uses. For example, in skin aging, sags and wrinkles can be caused by the loss of elastic fibers, including fibrillin-1. Compounds that increase production of fibrillin-1 can be identified, using the in vivo mouse model, and these compounds can be used to inhibit skin aging.

Targeting vectors were designed to create two lines of Fbn1 mutant mice. Targeting vectors were generated using C57BL/6 genomic DNA and were electroporated into Bruce 4 embryonal stem (ES) cells. ES cells were screened by Southern blotting for successful homologous recombination. Selected ES cells were injected into blastocysts to generate chimeras. Chimeras were bred to obtain germ-line transmission. Fbn1-targeted mice were genotyped by Southern blotting. The Neo gene used for selection was flanked by FRT sites and was removed by breeding targeted mice to C57BL/6 mice containing a transgene for FLPe recombinase. C57Bl/6 mice in which Cre recombinase was knocked into the Rosa 26 locus were bred to heterozygous Fbn1 floxed mice to yield mice in which the Fbn1 mutation was expressed in all cells. Floxed as well as mutant mice were generated by Ozgene Pty Ltd, Bentley DC, WA 6983, Australia.

To generate the first line of mice in which fibrillin-1 is truncated and tagged with eGFP, special lox sites were incorporated into the targeting vector. Cre-mediated recombination resulted in the inversion of the lox 66 and lox 77 sites, inverting at the same time the eGFP coding sequence into frame after exon 32, and the truncation of fibrillin-1 molecules. A polyglycine linker was engineered to invert between exon 32 and eGFP to facilitate proper folding of the last fibrillin domain and of eGFP. A line of mice called GT-8 ("green truncated" from founder mouse 8) was established and maintained on a C57BL/6 background. For this study, heterozygous GT-8 mice were bred to yield wildtype, heterozygous, and homozygous littermates for analyses. Genotyping was by PCR. To distinguish the wildtype Fbn1 allele, a primer pair (CCGTGGAATCTAAAACCT TGGAG (SEQ ID NO:4), and TGGGAATGATGTGGTGAGAGCC (SEQ ID NO:5)) was used to amplify intronic sequence between exons 34 and 35, yielding a 370 bp band from wildtype Fbn1 and no band from homozygous GT-8 Fbn1. Another primer pair (GTGGGTTCCATTAGAGCATTCATC (SEQ ID NO:6) and GGTGAGAGCCTGT ATTGTTTCCTC (SEQ ID NO:7)) was used to amplify sequences flanking the inverted exons 34 and 33, yielding a 591 bp fragment from GT-8 Fbn1 and no band from wildtype Fbn1. Heterozygous mice were identified by the presence of both the 370 bp wildtype band and the 591 bp inverted band.

A second line of mice was generated by Cre-mediated removal of Fbn1 exon 7, flanked by loxP sites, in all cells. This line of mice is called H1Δ (for hybrid 1 domain deletion), and it was maintained on a C57Bl/6 background. For this study, heterozygous H1Δ mice were bred to yield wildtype, heterozygous, and homozygous littermates for analyses. Genotyping was by PCR. An intronic primer pair (TTGGAATGACAGGCTGTGGCAC (SEQ ID NO:8) and TTCGCTGTGTTTCTACAAGGCAG (SEQ ID NO:9)) flanking exon 7 was used to amplify a 655 bp band from the deleted allele and a 1116 bp band from the wildtype allele. Mice heterozygous for the mutant allele displayed both bands, while wildtype or homozygous mice showed only a single band.

Fbn2+/− mice were bred to GT-8/+ to yield GT-8/+; Fbn2+/− mice. Doubly heterozygous mutant mice were bred to Fbn2−/− or Fbn2+/− female mice, and all progeny were genotyped by PCR. Fbn2 mutant mice were maintained on a 129/sv background. Fbn2 alleles were amplified by PCR using the following primer pair for exon 1: F2ex1F3 (TGTCTCCAGCCCTACTTCGT (SEQ ID NO:10)) and F2ex1R3 (CCTCGGAGTATTTCCTGCTG (SEQ ID NO:11)). This primer pair yielded a 231 bp Fbn2 exon1 band from the wild-type allele. Primers to amplify the neomycin gene were Neo-F (GGAGAGGCTATTC GGCTATGACTG (SEQ ID NO:12)) and Neo-R (CTCTTCGTCCAGAT-CATCCTGATC (SEQ ID NO:13)). This primer pair yielded a 436 bp band from the mutant allele which retained a neo cassette. For genotyping progeny, both exon 1 and neomycin primer pairs were utilized to distinguish between Fbn2 wildtype, heterozygous, and homozygous pups. In addition to these two different PCR approaches used to distinguish Fbn2 genotypes, Fbn2 null mice consistently displayed syndactyly.

Figure 1B:
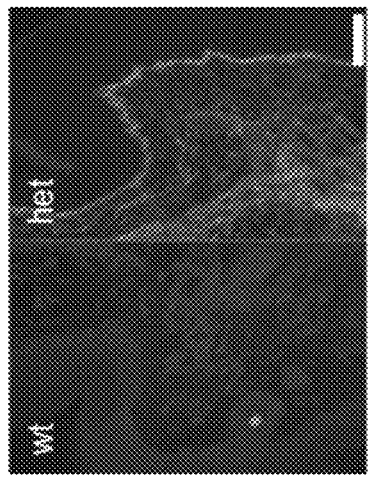
Figure 1C:
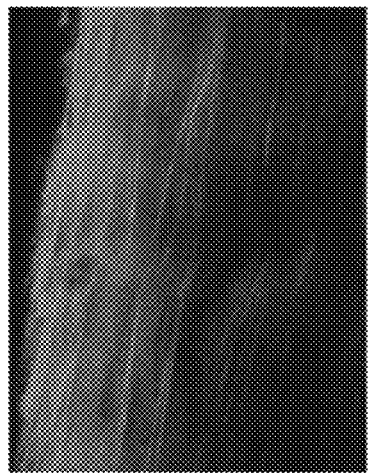
Figure 1D:
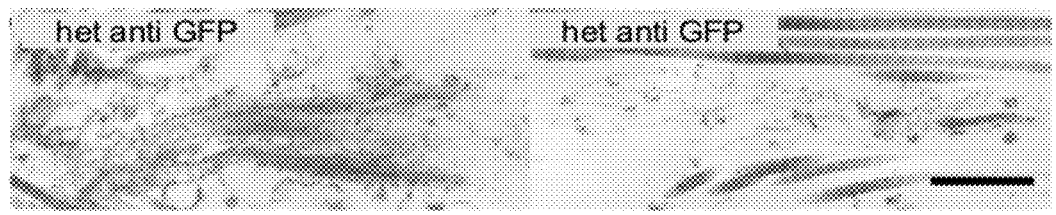
Figure 1E:
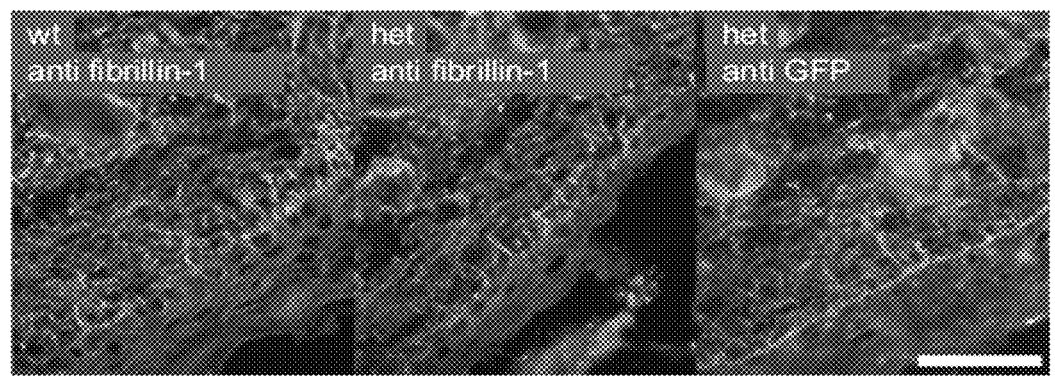
Figure 1F:
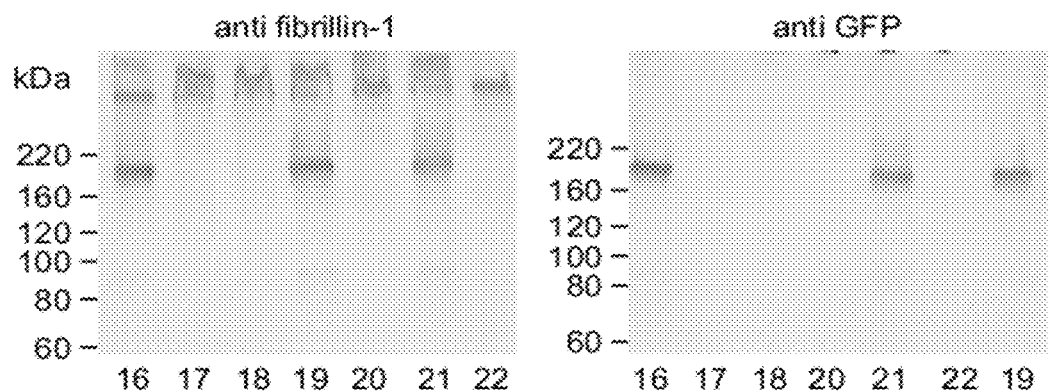

A diagram of the locus targeted in the GT-8 mouse model is shown in FIG. 1A. The truncated molecule contains the N-terminal half of fibrillin-1, ending with calcium-binding EGF-like domain #17 followed by a polyglycine linker and eGFP. A line of heterozygous mice, called GT-8/+, which expresses mutant Fbn1 in all cells, was characterized. The incorporation of the truncated fibrillin-1 into typical fibrillin-1 microfibril patterns were easily visualized because of the eGFP tag. Green fluorescence was observed by whole mount confocal microscopy of tendon (FIG. 1B) and by epifluorescence microscopy of unstained, PBS treated skin sections (FIG. 1C). Electron microscopic immunolocalization demonstrated antibodies specific for GFP bound to fibrillin microfibrils present in elastic fibers and in bundles of microfibrils without amorphous elastin (FIG. 1D). Anti-GFP immunolocalization was equivalent to anti-fibrillin-1 immunolocalization in heterozygous early postnatal (P3) skin, and this was equivalent to anti-fibrillin-1 immunolocalization in wildtype littermate skin (FIG. 1E). Immunoblotting of truncated fibrillin-1 secreted into the medium of cultured fibroblasts was equivalent to wildtype fibrillin-1 (FIG. 1F). Based on these data, it was concluded that mutant fibrillin-1 is incorporated into microfibrils and does not interfere with the assembly of microfibrils.

Figure 2A:
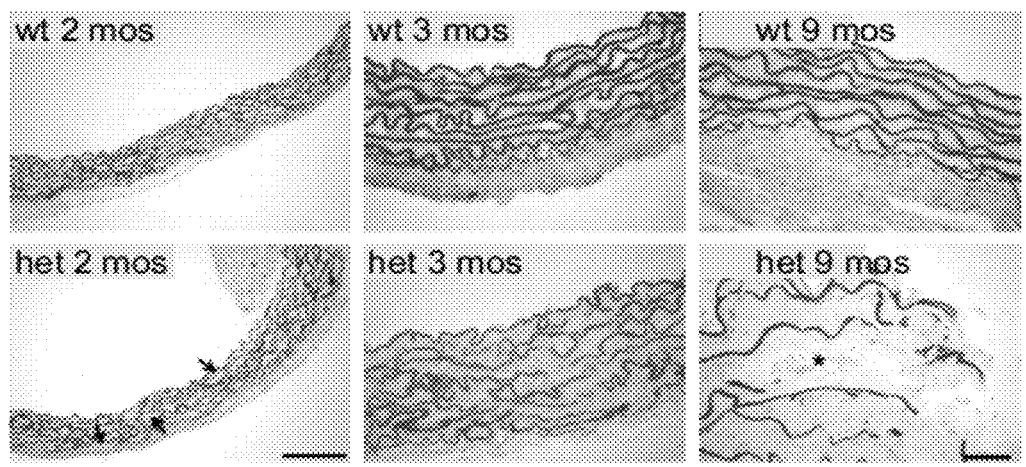
FIGS. 2A-2D. (A) Aortic root morphology was evaluated in wildtype and heterozygous GT-8 littermates at various timepoints. At 2 months of age, breaks in the elastic lamellae could easily be found in heterozygous mice (arrows). These breaks in the elastic lamellae became more severe by 3 months of age in heterozygous mice. By 9 months of age, breaks in the heterozygous lamellae could be found across whole planes of the aortic wall, resulting in infiltration of blood cells (*) into the smooth muscle media. Scale bars=100 μm. (B) Unstained, PBS treated P3 wildtype and heterozygous GT-8 aortic root demonstrated eGFP-fibrillin-1 throughout the width of the heterozygous elastic lamellae. Anti-fibrillin-1-stained wildtype and heterozygous aortic root sections show red immunofluorescence in the adventitia and red or yellow (merged green and red) immunofluorescence in the internal elastic lamina and on the surfaces of the elastic lamellae. However, anti-fibrillin-1 staining does not appear to fully penetrate into the elastic lamellae. Scale bar=50 μm. (C) Unstained PBS treated sections of aorta from E16 and P3 heterozygous GT-8 mice revealed green fluorescence, visible at E16, which accumulates from E16 to the early postnatal period. Scale bar=20 μm. (D) Peripheral blood vessels also accumulated large amounts of fibrillin-1 after birth and demonstrated increasing amounts of green fluorescence in heterozygous mice during the early postnatal period. Scale bar=50 μm.
Figure 2B:
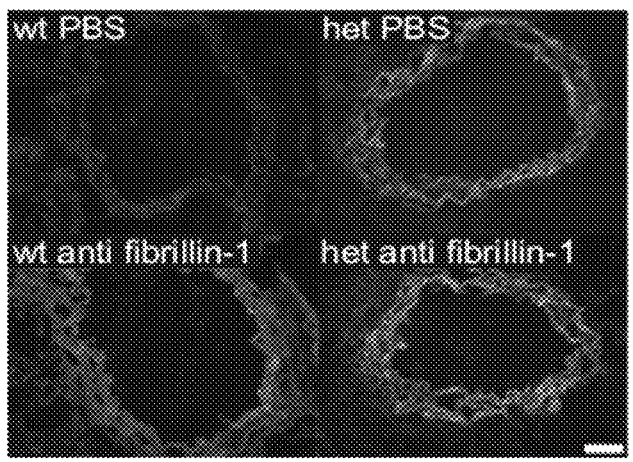
Figure 2C:
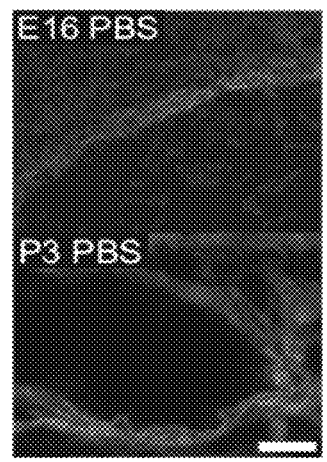
Figure 2D:
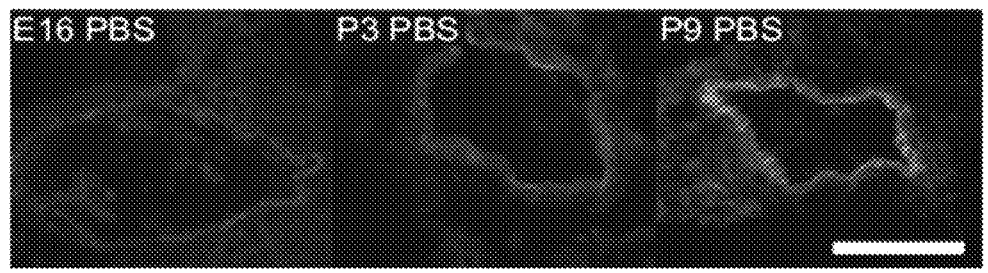

In GT-8/+ mice, fragmentation of the aortic elastic lamellae was observed from 2 months of age, becoming progressively more severe with increasing age (FIG. 2A). In contrast to typical elastic fibers in the dermis and perichondrium, microfibrils are not easily visualized by electron microscopy on the surfaces of the aortic elastic lamellae, which are therefore morphologically unique elastic fiber structures. In order to determine the extent to which fibrillin microfibrils contribute to aortic elastic lamellae, unstained, PBS treated sections of GT-8/+ aorta were visualized. Green fluorescence was emitted from the full width of the elastic lamellae in GT-8/+ mice, revealing that fibrillin-1 is inside the amorphous elastin as well as on the surface of the lamellae (FIG. 2B). GT-8/+ mice also showed that the highest concentrations of fibrillin-1 are accumulated in blood vessels, compared with all other tissues examined. Green fluorescence was visible in the aorta by E16, becoming progressively more fluorescent through early postnatal life (FIG. 2C). In peripheral blood vessels, increasing green fluorescence from E16 through P9 was noted (FIG. 2D). Accumulation of green fluorescence in other tissues in recognizable microfibrillar patterns was not seen until after 1 month of age, even though immunostainings with anti-fibrillin-1 and anti-GFP in these tissues suggested equivalent and abundant wildtype and mutant fibrillin-1 (FIG. 1). These data demonstrate several novel results: (1) fibrillin-1 is most abundant in the aorta and other blood vessels, compared to other tissues like skin, tendon, and perichondrium; (2) fibrillin-1 concentrations increase during the postnatal period and vary according to tissue; and (3) mutant fibrillin-1 is incorporated throughout the width of the elastic lamellae, resulting in aortic disease.

Microfibril assembly and stability was also tested in H1Δ Mice. The first hybrid domain in fibrillin-1 contains a free cysteine residue and also mediates binding interactions between fibrillin-1 and Latent TGFβ Binding Proteins (LT-BPs). H1Δ fibrillin-1, which is shorter than wildtype fibrillin-1, was tested to determine if the mutation would perturb microfibril assembly in vivo. In heterozygosity, H1Δ mice tested the hypothesis that fibrillin-1 molecules are required to be in perfect register for microfibril assembly and stability. Homozygous H1Δ mice tested whether the free cysteine present in the first hybrid domain is required for microfibril assembly. Heterozygous and homozygous H1Δ mice were born according to Mendelian frequencies, and both mutant genotypes survived well past 1 year of age. All other homozygous Fbn1 mutant mice die in the early postnatal period, including GT-8 homozygotes, with the exception of homozygous tight skin or tsk mice, which die during early embryogenesis. Therefore, the compatibility of a homozygous Fbn1 mutation with a normal life span was surprising.

Figure 8A:
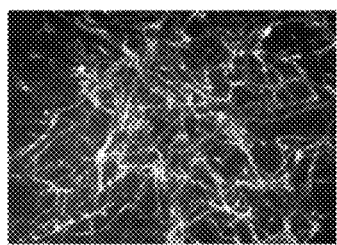
FIG. 8A-8I: In vitro assembly of mutant fibrillin-1. Fibroblasts were established from early postnatal littermate skin. GT-8 wildtype (A,D), heterozygous (B,E) and homozygous (C,F) cultures were stained with anti-fibrillin-1 (pAb 9543) (A,B,C) or with anti-GFP (D,E,F). Results showed that, in contrast to wildtype fibroblasts, heterozygous cells assembled fewer fibrillin-1 positive fibrils and that truncated fibrillin-1 was assembled into fibrils. Homozygous fibroblasts failed to assemble fibrillin-1 fibrils in vitro. After immunostaining with anti-fibrillin-1, H1Δ wildtype (G), heterozygous (H), and homozygous (I) demonstrated abundant fibrillin-1 fibrils. Scale bar=50 μm.
Figure 8B:
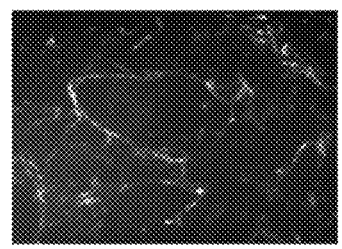
Figure 8C:
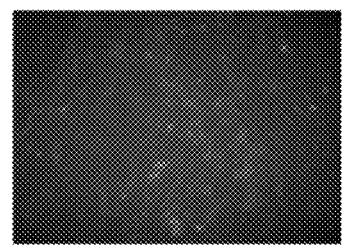
Figure 8D:
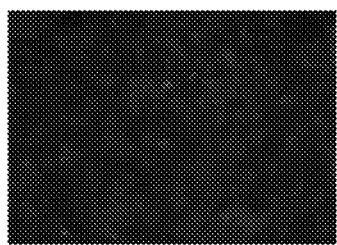
Figure 8E:
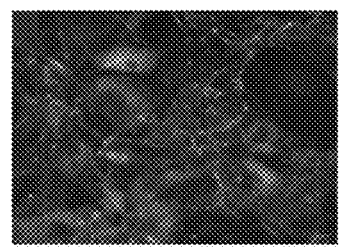
Figure 8F:
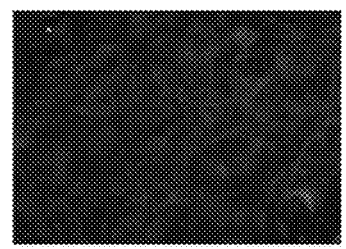
Figure 8G:
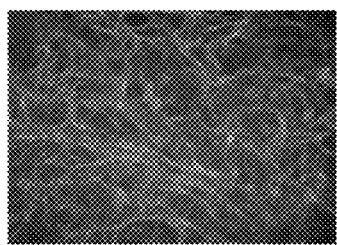
Figure 8H:
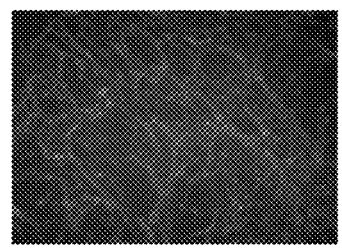
Figure 8I:
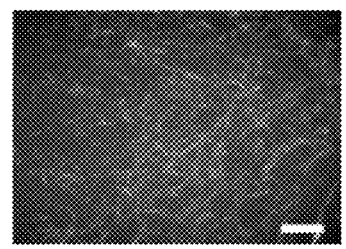
Figure 9A:
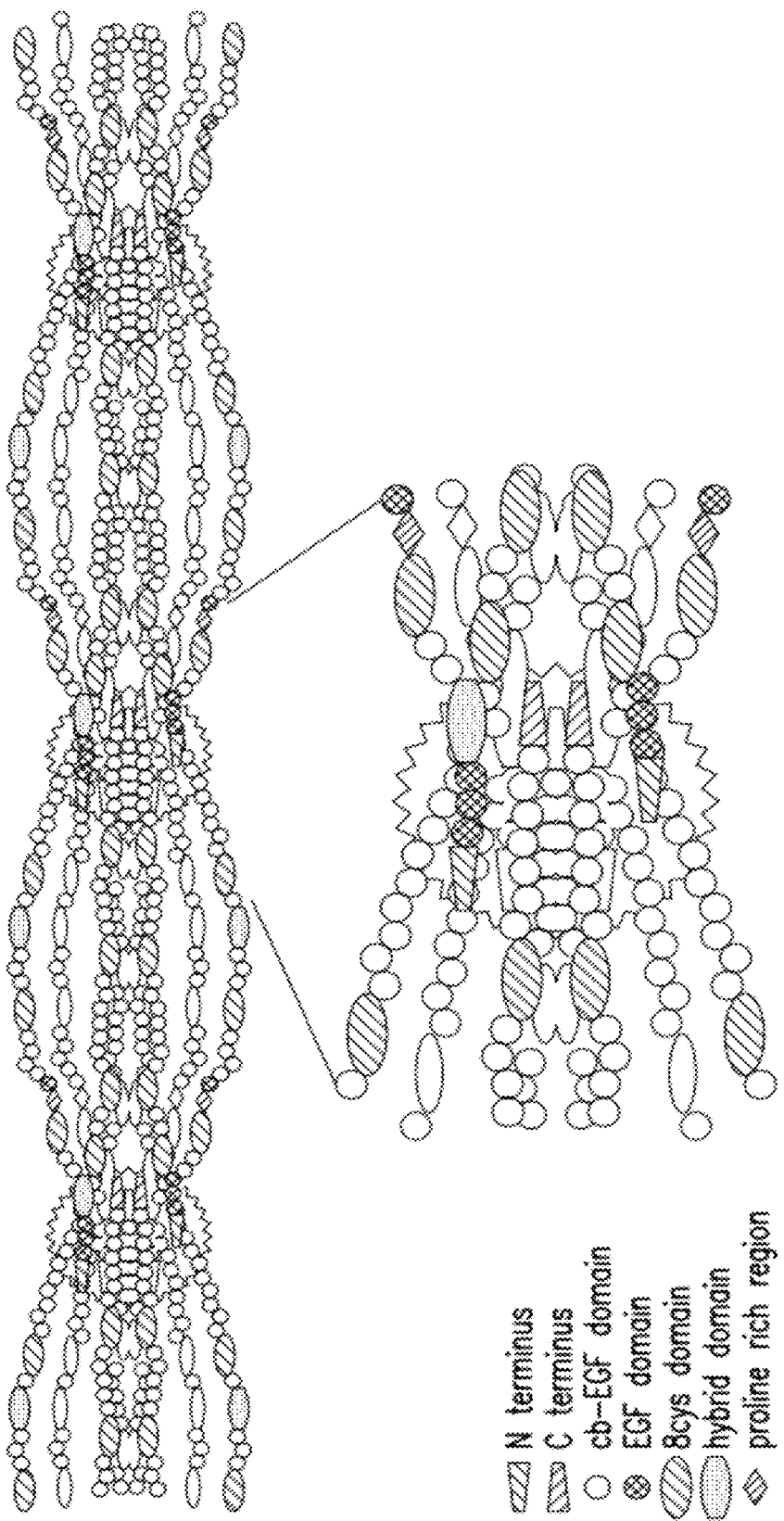
FIG. 9A-9B: Microfibril structure in H1Δ mutant mice. (A) Deletion of the first hybrid domain shortens the length of fibrillin-1, which may result in defects in microfibril assembly or stability if perfect registration of fibrillin-1 molecules is required. The cartoon depicts incorporation of shortened H1Δ fibrillin-1 molecules into a polymeric microfibril structure with wildtype fibrillin-1 molecules. The inset is a larger view of the microfibril close to the first hybrid domain. Fibrillin-1 molecules are in color, while the hypothesized core of fibrillin-2 molecules is depicted in black. The stagger and orientation of fibrillin molecules is according to Kuo et al., JBC, 282; 4007-4020 (2007). (B) Fibrillin-1 immunostaining of P1 and P10 wildtype, heterozygous and homozygous H1Δ skin demonstrated no differences in abundance or pattern of microfibril fiber bundles. Fibrillin-2 immunostaining of P10 wildtype, heterozygous and homozygous H1Δ skin did not reveal fibrillin-2 in H1Δ mutant mice, indicating that microfibril structure is stable in the mutants during the early postnatal period. Scale bar=50 μm
Figure 9B:
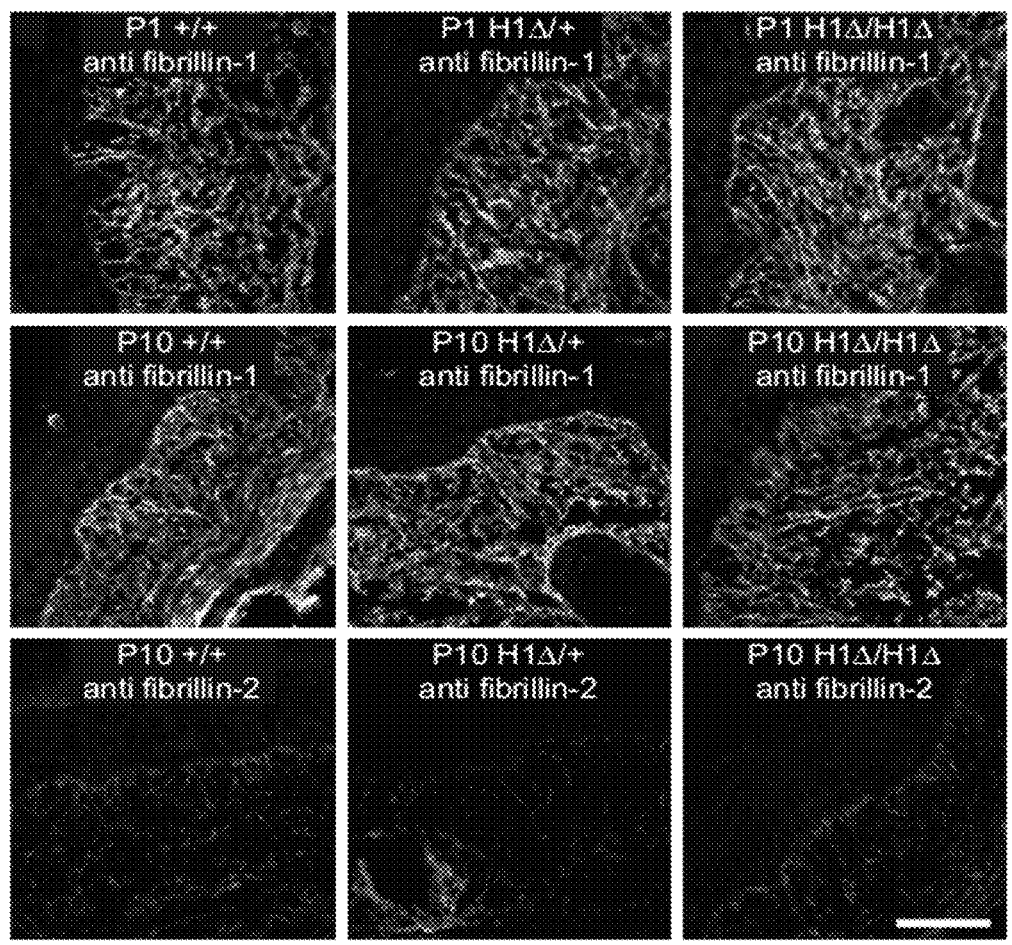
Figure 10:
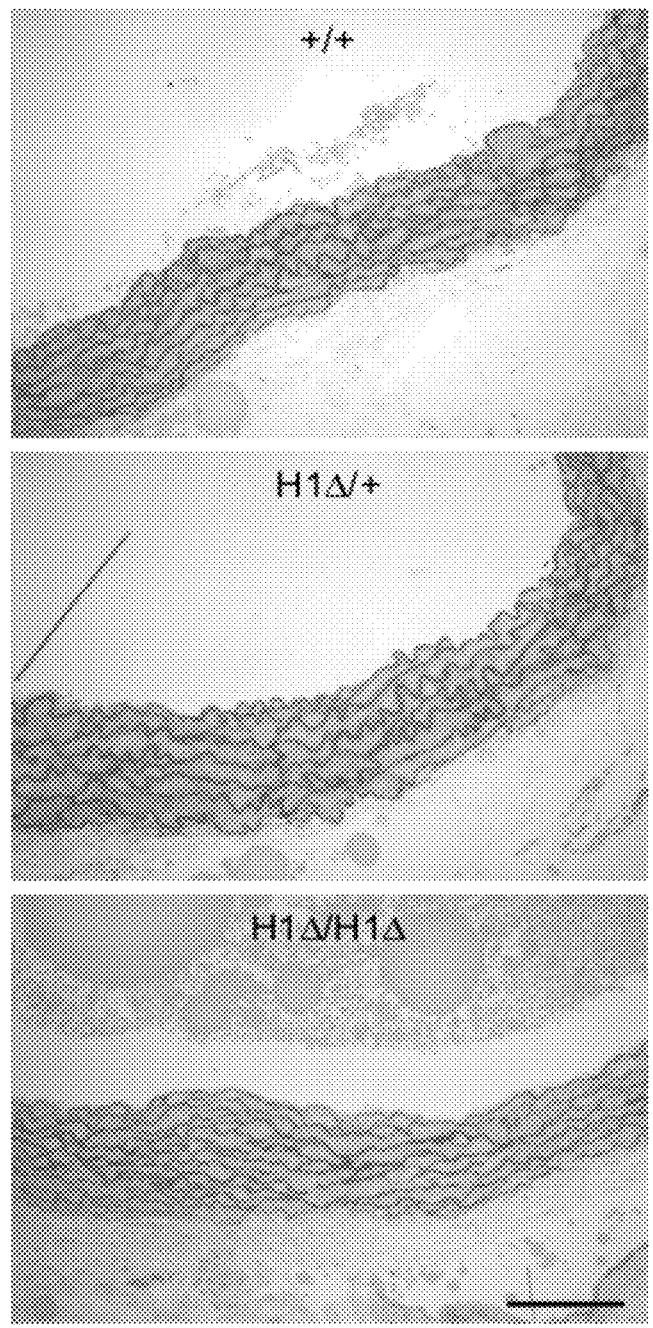
FIG. 10: Aortic root morphology in H1Δ mutant mice. Aortic root morphology in 15 month wildtype, heterozygous and homozygous mice showed minimal fragmentation of the elastic lamellae. Scale bar=100 μm.
Figure 11A:
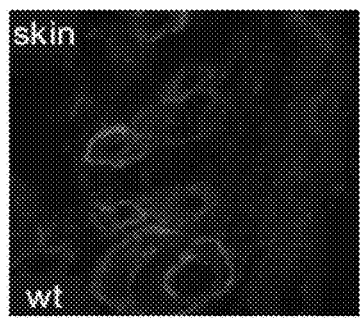
FIG. 11A-11H: Fibrillin-2 microfibrils are unmasked in mouse Fbn1 null tissues. P8 wildtype (A, C, E, G) and Fbn1−/− (B, D, F, H) littermate sections were stained with pAb 0868, specific for fibrillin-2. Fibrillin-2 immunostaining was mostly negative in wildtype sections of skin (A) and skeletal muscle (C) at this time; there was weak fibrillin-2 immunostaining in wildtype sections of tendon (E) and perichondrium (F). However, in Fbn1−/− sections, fibrillin-2 immunostaining was revealed in typical tissue-specific fibrillin microfibril patterns (B, D, F, H). Scale bar=50 μm.
Figure 11B:
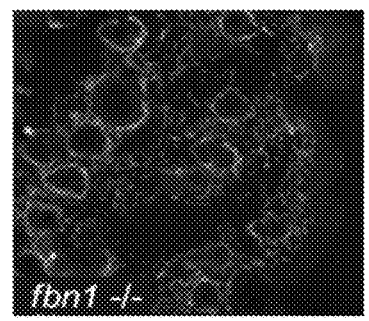
Figure 11C:
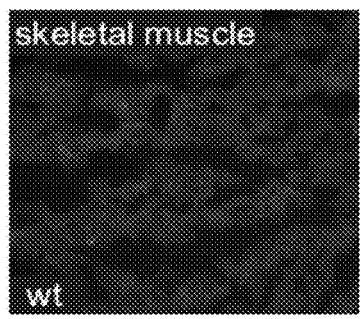
Figure 11D:
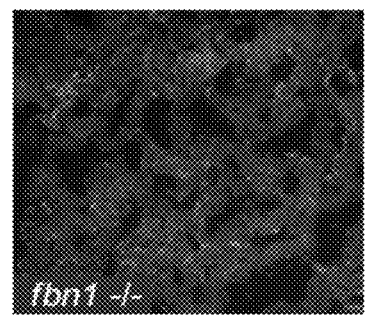
Figure 11E:
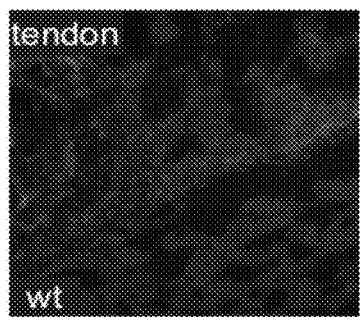
Figure 11F:
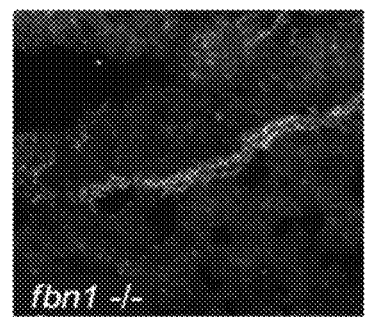
Figure 11G:
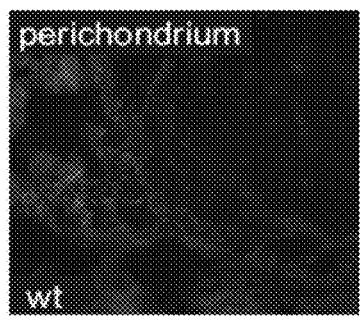
Figure 11H:
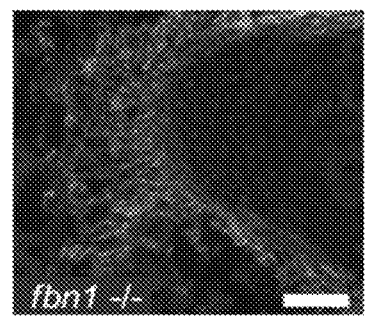

Examinations of microfibril assembly in vitro showed that H1Δ fibrillin-1 did not interfere with fibrillin-1 fibril assembly in heterozygosity (FIG. 8H, compared to wildtype littermate fibroblasts in FIG. 8G) and that homozygous H1Δ fibrillin-1 could form fibrillin-1 fibrils (FIG. 8I). Comparison of fibrillin-1 microfibril immunostaining in various tissues at different early postnatal timepoints confirmed these in vitro observations. FIG. 9B shows apparently normal fibrillin-1 microfibril staining patterns in skin at P1 and at P10, indicating normal assembly of fibrillin-1 in vivo. In addition, P10 mutant skin failed to show fibrillin-2 immunostaining, indicating that microfibril structure is stable during the early postnatal period, in contrast to GT-8 mutant mouse tissues. In addition, examination of aortic elastic lamellae did not show significant fragmentation, even at timepoints greater than 1 year of age (FIG. 10), and ultrastructural analyses showed no visible differences in microfibril structure.

Example 1.2 Antibody Detection of Fibrillin Targets

Figure 3A:
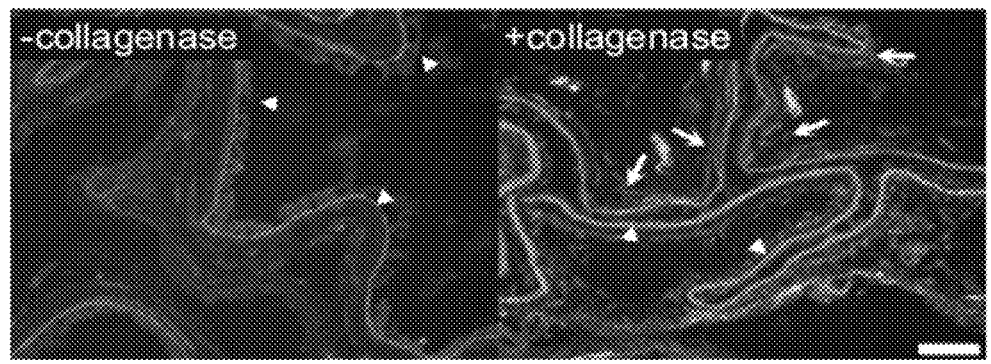
FIGS. 3A-3D. (A) Sections of human amnion, which contains bundles of fibrillin microfibrils without amorphous elastin, were stained with monoclonal antibodies specific for fibrillin-2. Undigested (-collagenase) sections showed fibrillin-2 immunofluorescence only weakly in the amniotic epithelial basement membrane (arrowheads). In contrast, fibrillin-1 antibodies also stained microfibril bundles (data not shown). Digested (+collagenase) sections stained with fibrillin-2 antibodies revealed increased staining of the basement membrane (arrowheads) as well as abundant staining of the fibrillin microfibril bundles. Scale bar=50 μm. (B) Heterozygous GT-8 aortic root sections were stained with pAb 0868, specific for fibrillin-2. Undigested (0 mg/ml) sections showed eGFP-fibrillin-1 fluorescence of the elastic lamellae, but no red fibrillin-2 immunofluorescence. With increasing concentrations of enzyme (0.05 mg/ml-0.2 mg/ml), red or yellow (merged green and red signals) fibrillin-2 immunofluorescence was revealed and eGFP-fibrillin-1 fluorescence was lost. Scale bar=20 μm. (C) P8 wildtype and Fbn1−/− littermate sections were stained with pAb 0868, specific for fibrillin-2. Fibrillin-2 immunostaining was mostly negative in wildtype sections of skin, except around hair follicles, and skeletal muscle at this postnatal time point; there was weak fibrillin-2 immunostaining in wildtype sections of tendon and perichondrium. However, in Fbn1−/− sections, fibrillin-2 immunostaining was revealed in typical tissue-specific fibrillin microfibril patterns. Scale bar=50 μm. (D) Based on these data, it was proposed that fibrillin-2 molecules (molecules drawn in black) form a core within the microfibril and that fibrillin-1 molecules, with their domain modules shown in color, constitute the outer shell of the microfibril.
Figure 3B:
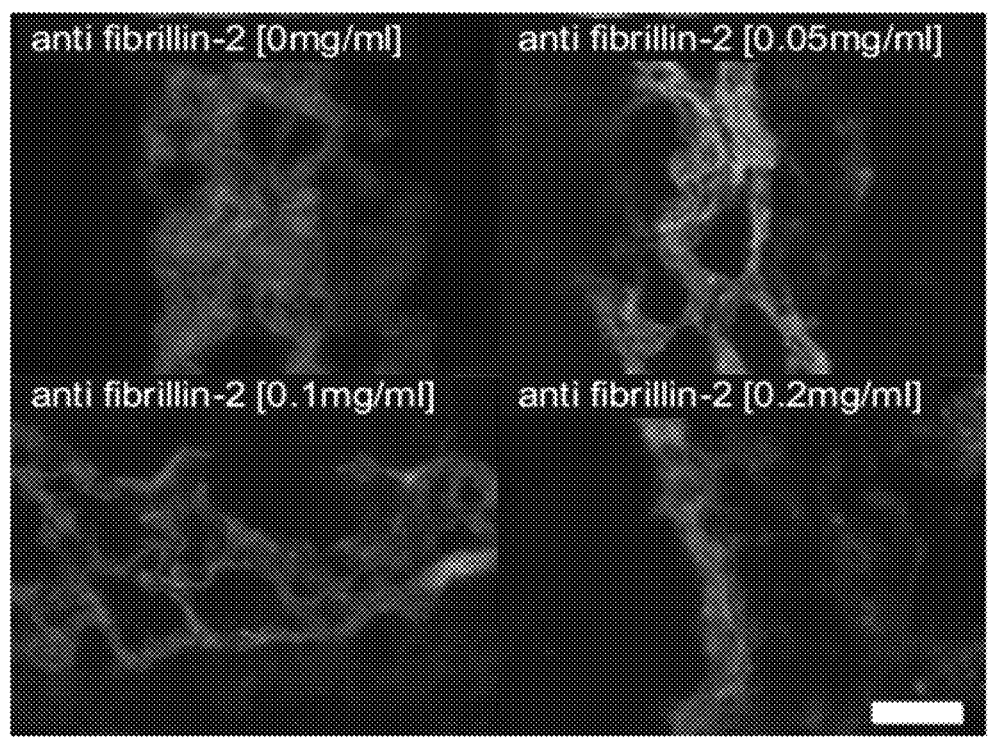
Figure 3C:
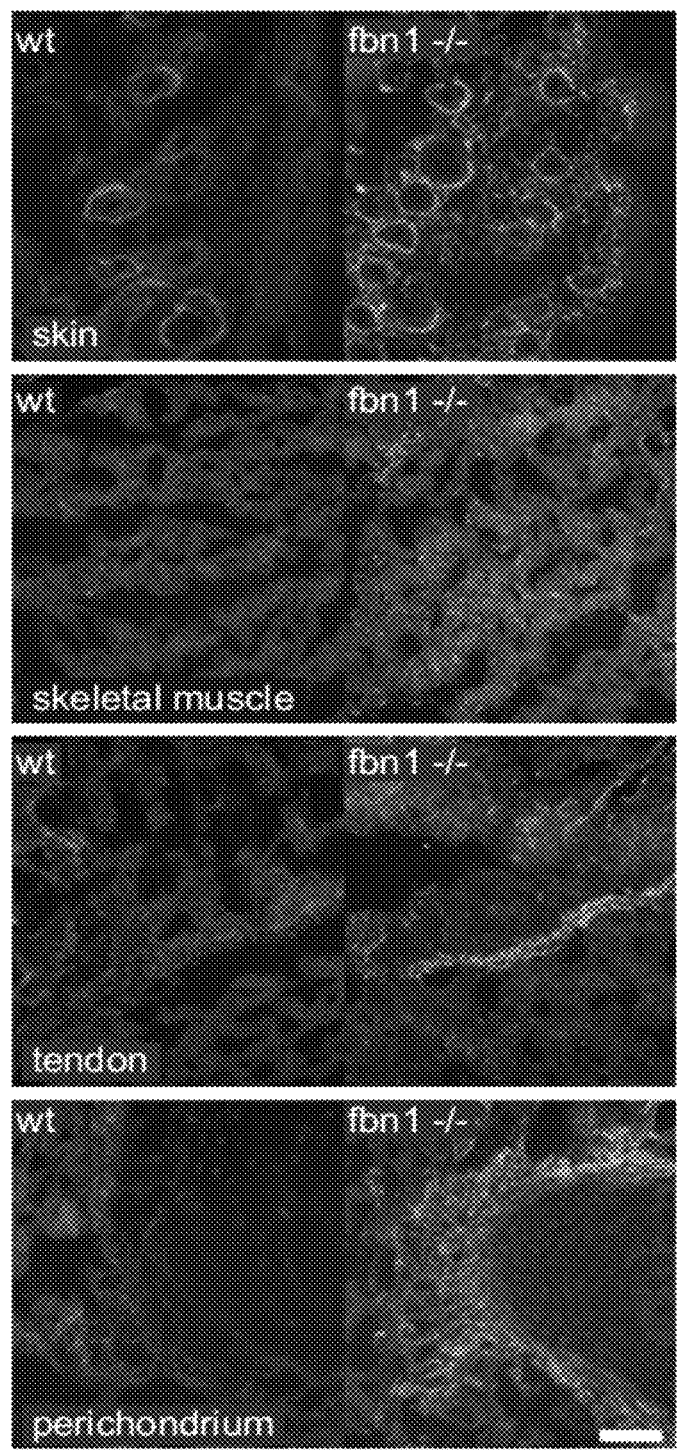
Figure 3D:
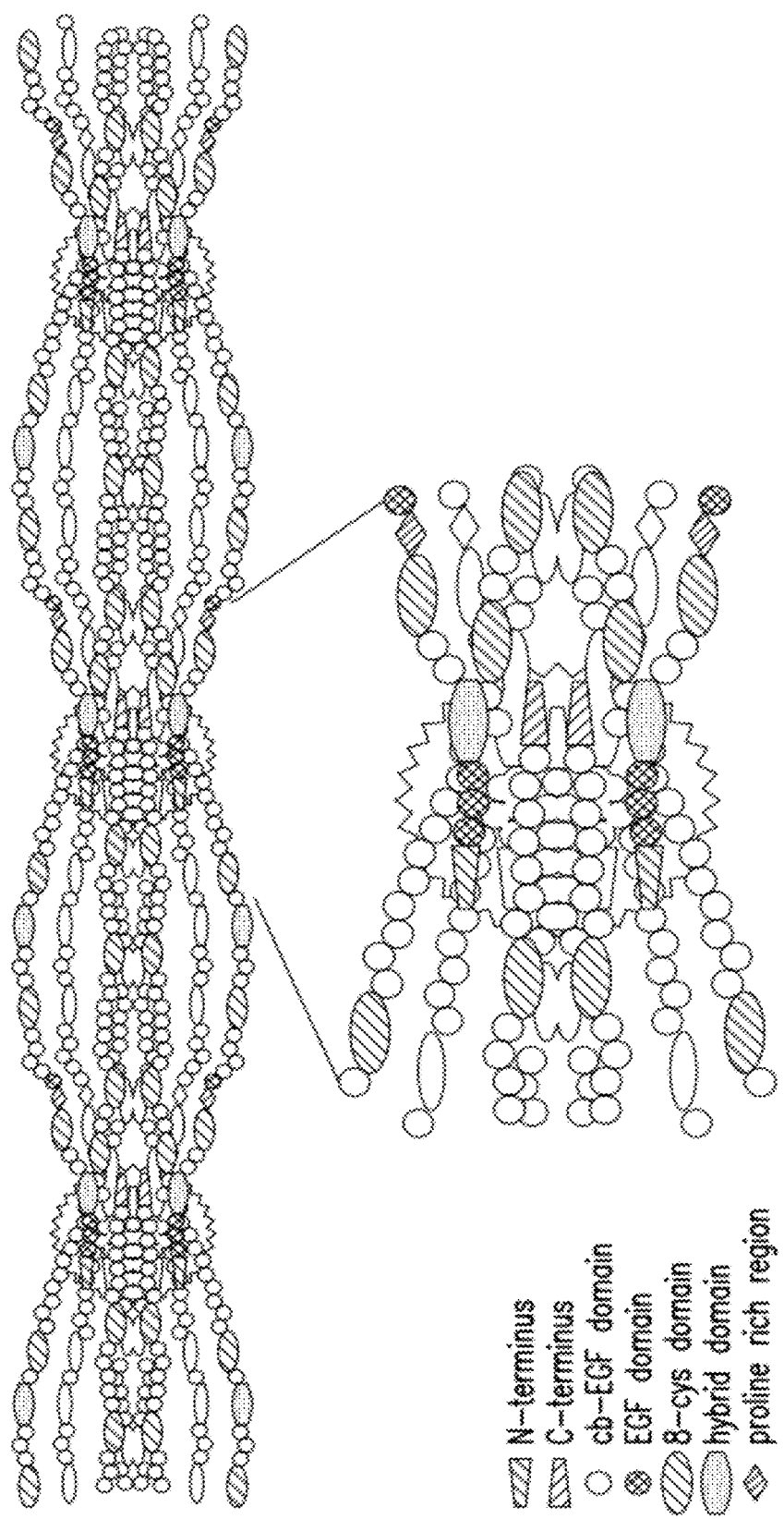

In order to determine whether incorporation of the mutant fibrillin-1 targets microfibrils for proteolytic degradation, a number of separate approaches were used. First, whether fibrillin-2 can be revealed in microfibrils after protease digestion and thus serve as a marker for microfibril fragmentation was tested. Fetal microfibrils are composed of heteropolymers of fibrillin-1 and fibrillin-2). Since expression of Fbn2 is largely limited to the fetal period and immunolocalization of fibrillin-2 protein is not apparent in most postnatal tissues, it is reasoned that fibrillin-2, generated during fetal development, forms a core of molecules masked by the subsequent accumulation of microfibril proteins, especially by fibrillin-1. As evidence of this, tissue sections were digested with crude collagenase prior to immunostaining with fibrillin-2 antibodies. Human amnion was selected for the first experiments, since this tissue contains bundles of fibrillin microfibrils without elastin. FIG. 3A shows that digestion of human amnion with crude collagenase reveals fibrillin-2 fibrils that were masked in the undigested sections. FIG. 3B shows that fibrillin-2 can be unmasked from within the aortic elastic lamellae. Undigested aortic root sections showed no red fibrillin-2 immunofluorescence. As increasing concentrations of crude collagenase were incubated on the sections, fibrillin-2 immunostaining was progressively revealed, and eGFP-fibrillin-1 fluorescence was progressively lost. It was previously shown that crude collagenase cleaves fibrillin-1 at multiple specific sites, therefore, molecules of fibrillin-2 are inside, and molecules of fibrillin-1 are on the surface, of the microfibrils. Analyses of microfibrils in postnatal wildtype and Fbn1 null mouse tissues provide evidence of this structure. FIG. 3C shows that fibrillin-2 immunostaining is abundant in Fbn1 null mouse tissues, while littermate wildtype mouse tissues are unstained. These results indicate that fibrillin-1 masks fibrillin-2 in wildtype tissues. FIG. 3D shows a cartoon depicting the model outlined above.

Figure 16:
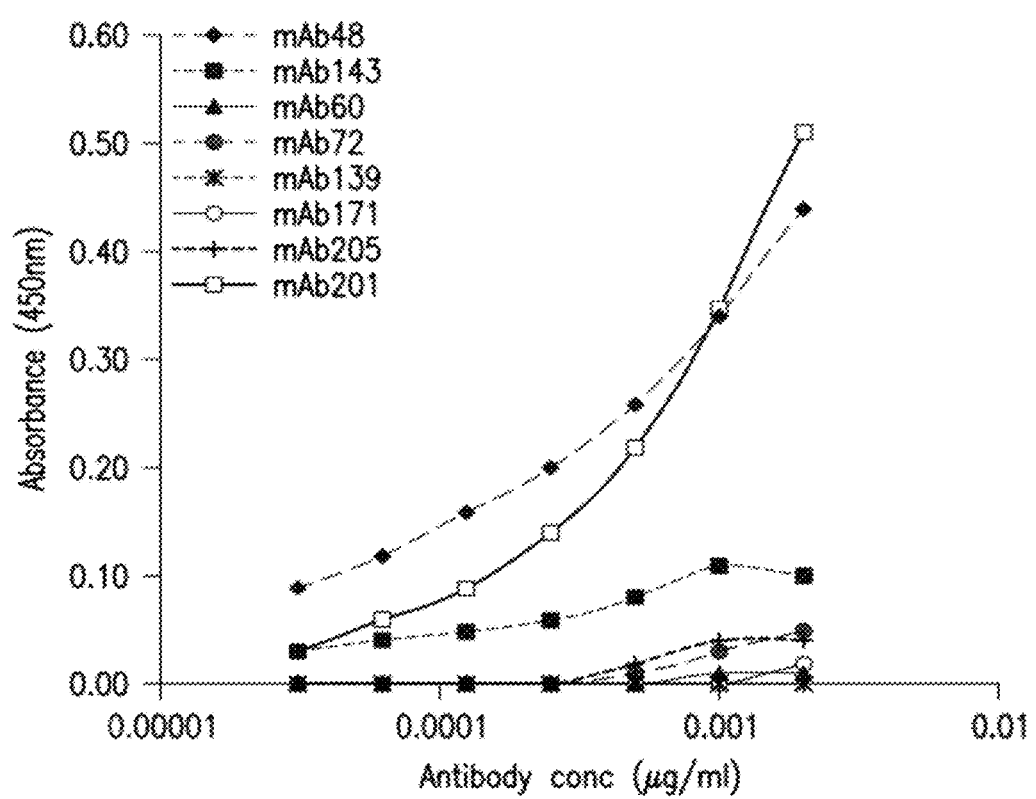
FIG. 16: Detection of fibrillin-2 epitopes in microfibrils extracted from human amnion. Guanidine-extracted microfibrils were used to coat ELISA plates. Titrations of fibrillin-2 mAbs 48, 143, 60, 72, 139, 171, and 205 and fibrillin-1 mAb 201 were tested. Fibrillin-2 epitopes recognized by mAb 48, and possibly also by mAb 143, were revealed in guanidine-extracted microfibrils. However, cryptic epitopes recognized by mAbs 60, 72, 139, 171, and 205 remained cryptic even after treatment with 6M guanidine. mAb 201 served as a control in these experiments.

In order to determine whether fibrillin-2 epitopes could be revealed by removal of noncovalently bound microfibril components, microfibrils were tested after extraction from human amnion with 6M guanidine. Guanidine-extracted microfibrils were adsorbed to ELISA plates. Fibrillin-2 mAbs 48, 143, 60, 72, 139, 171, and 205 were titrated and tested for reactivity. Fibrillin-1 mAb 201 was titrated and used as a control. Guanidine extracted microfibrils reacted well with both mAb 201 and mAb 48 and weakly with mAb 143, while other fibrillin-2 mAbs were unreactive (FIG. 16). These data suggest that certain fibrillin-2 epitopes masked in amnion tissue (mAb 48 and mAb 143) may be unmasked by removing non-covalently bound microfibril associated proteins and/or by altering the quarternary structure of the microfibril with denaturants. However, all other fibrillin-2 epitopes remained masked in the presence of 6M guanidine. Since multiple fibrillin-1 epitopes were previously shown to be retained in guanidine extracted microfibrils, these results are interpreted to indicate that the cryptic fibrillin-2 epitopes are masked by the structure of the microfibril.

Homopolymeric fibrillin-2 microfibrils are exposed in early postnatal fibrillin-1 (Fbn1) null tissues. Microfibrils in postnatal wildtype mouse tissues, as in human tissues, were not well stained with pAb 0868, specific for fibrillin-2 domains contained in rF37. In a second approach to determine the postnatal fate of fibrillin-2, fibrillin-2 is examined in Fbn1 null mouse tissues. In contrast to wildtype littermate mouse tissues, abundant pAb 0868 immunoreactive fibrillin-2 microfibrils were observed in all newborn and early postnatal Fbn1 null tissues. FIG. 11 shows that fibrillin-2 microfibril staining is revealed in the skin, skeletal muscle, tendon, and perichondrium of P8 Fbn1 null mice, compared to wildtype littermate control sections. These results indicate that fibrillin-1 molecules or fibrillin-1 associated molecules mask fibrillin-2 epitopes in postnatal tissues.

Figures 12A, 12B:
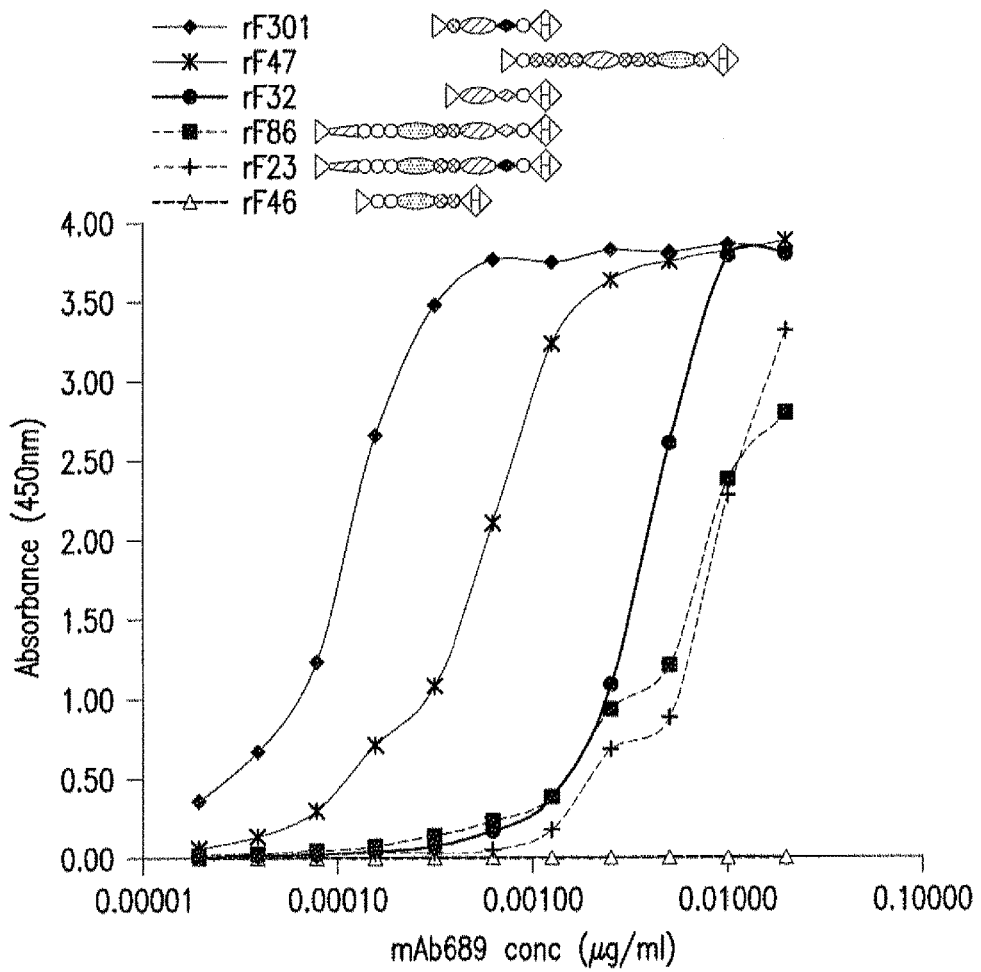
FIG. 12A-12B: mAb 689 binds to an epitope in EGF4 in all three fibrillins. When tested in ELISA (A), mAb 689 reacted with rF301, the recombinant fibrillin-3 peptide used to generate this mAb. mAb 689 also reacted with recombinant fibrillin-1 and fibrillin-2 peptides containing EGF4, but not with peptides missing EGF4. Of the 4 domains contained in rF301, rF47 contains only EGF4, and mAb 689 reacted well with rF47. Similarly, mAb 689 reacted well with rF20, a fibrillin-1 recombinant peptide whose N-terminal domain is EGF4 (data not shown). (B) Identical residues in the amino acid sequences of EGF4 in fibrillin-1, fibrillin-2, and fibrillin-3 are shadowed.

In order to extend the preceding findings beyond fibrillin-1 and fibrillin-2 mAb 689 was generated using rF301 (depicted in FIG. 7B), a recombinant human fibrillin-3 polypeptide that spans cbEGF1, 8cys1, the proline/glycine rich region, and EGF4. mAb 689 recognizes rF301 as well as polypeptides containing the homologous region from fibrillin-1 and fibrillin-2. These include rF23 and rF30 (fibrillin-1) and rF86 and rF32 (fibrillin-2) (FIG. 5A). Using additional polypeptides as coated substrates, ELISAs were performed in order to more precisely map the epitope recognized by mAb 689. FIG. 12A shows that mAb 689 binds to peptides containing the fourth EGF domain, but not to peptides that lack this domain. mAb 689 reacted well with the fibrillin-1 peptide rF20 and the fibrillin-2 peptide rF47 (FIG. 12A), which contain EGF4 but lack the preceding domains. Based on these data, it is concluded that mAb 689 is a pan-fibrillin antibody that binds to an epitope contained largely in EGF4.

In addition to human fibrillin, mAb 689 recognizes mouse fibrillin (FIGS. 13 and 14). The primary structure of human and mouse fibrillin-1 EGF4 is identical, as is the primary structure of human and mouse fibrillin-2 EGF4. However, only 25 of the 41 residues are identical in fibrillin-1 and fibrillin-3 EGF4; whereas 31 of the 41 residues are identical in fibrillin-2 and fibrillin-3. 22 residues are identical in all three fibrillins. FIG. 12B shows the region of identity in the EGF4 sequence. This region of identity clusters around the residues predicted to form the second strand of an antiparallel β sheet, which likely forms the core structure of EGF4. The mAb 689 epitope is stabilized by disulfide bonds, since reduction abolishes immunoreactivity.

Figure 13A:
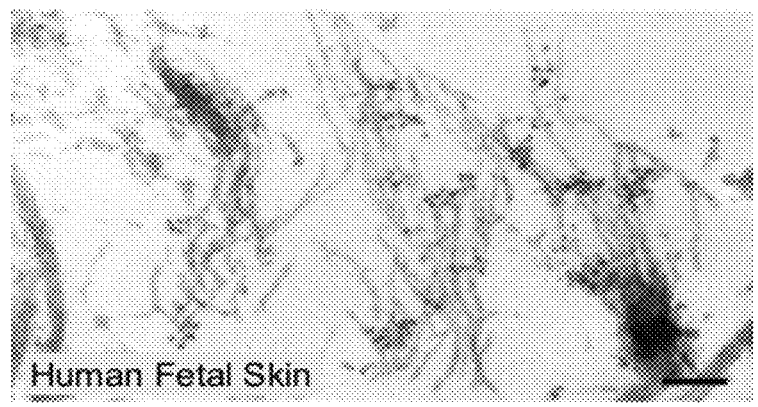
FIG. 13A-13D: Immunolocalization of mAb 689 to fibrillin microfibrils and to basement membranes. Immunogold labeling was observed on microfibrils in 16 week human fetal digit skin (A), but little to no labeling was found when 21 year old human skin was tested (B). Similarly, P0 wildtype mouse skin demonstrated relatively little labeling of microfibrils (C), whereas the retinal pigment epithelial cell basement membrane of E13.5 wildtype mouse eye was well labeled (D). Scale bars=100 nm for (A) and (B); 200 nm for (C); 500 nm for D.
Figure 13B:
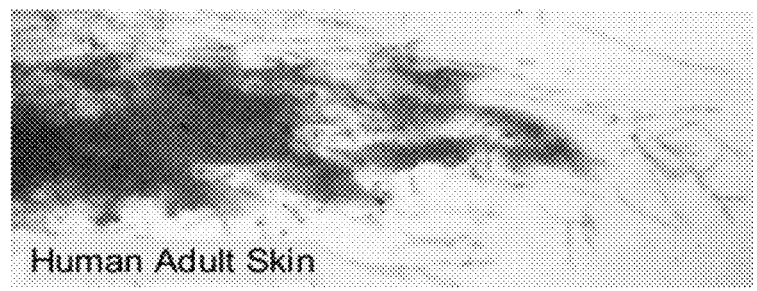
Figure 13C:
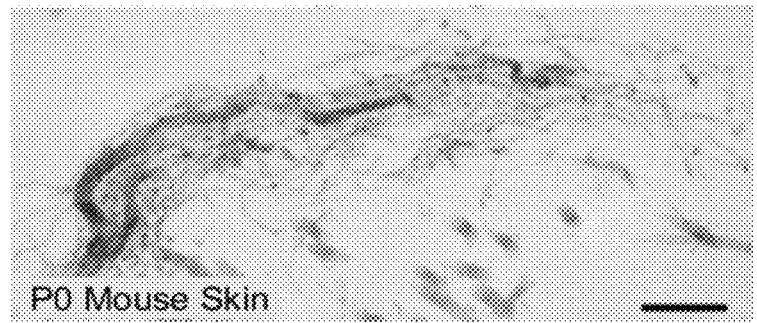
Figure 13D:
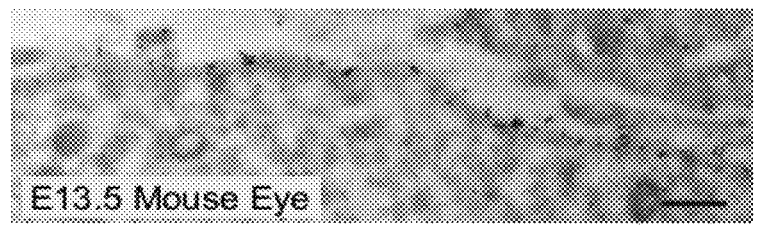

Since fibrillin-1, fibrillin-2, and fibrillin-3 antibodies have been immunolocalized to fetal microfibrils, it was expected that mAb 689 would label heteropolymeric fetal microfibrils. Microfibrils (FIG. 13A) and basement membranes (FIG. 13D) were well labeled by mAb 689 in fetal tissues. However, mAb 689 failed to label microfibrils in adult human skin (FIG. 13B), and labeling of P0 wildtype mouse was sparse, even though microfibrils were abundant (FIG. 13C). Poor reactivity with adult or early postnatal microfibrils was unexpected, since mAb 689 binds well to fibrillin-1 in ELISA (FIG. 13A).

Figure 14A:
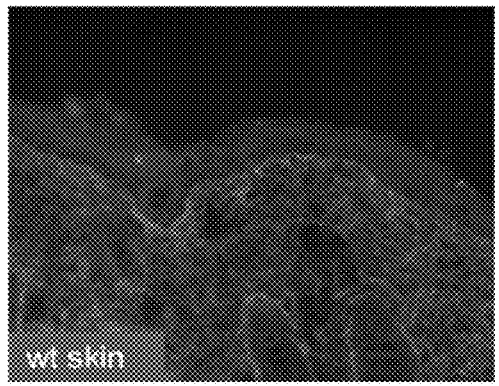
FIG. 14A-14F: Tissue-specific differences in the availability of the mAb 689 epitope. Postnatal wildtype mouse tissues showed relatively little immunostaining when mAb 689 was used. Dermal microfibrils in P8 wildtype skin were very weakly stained with mAb 689 (A). In contrast, mAb 689 staining of fibrillin-2 microfibrils in Fbn1−/− skin demonstrated typical fibrillin microfibril patterns in the dermis and in the dermal-epidermal junction (B). Fibrillin-1 microfibrils in P9 Fbn2−/− perichondrium were relatively unstained (C), indicating that the mAb 689 epitope is cryptic in fibrillin-1 microfibrils. However, when Fbn2−/− tissue sections were digested with crude collagenase, mAb 689 stained fibrillin-1 microfibrils in the perichondrium of Fbn2−/− tissue sections (D). Undigested sections of P9 Fbn2−/−spinal cord displayed abundant microfibril bundles that stained with mAb 689 (E). Fibrillin-2 mAb 171 stained peripheral nerves in undigested tissue sections of 20 month human extra digit (F). Scale bars=50 μm.
Figure 14B:
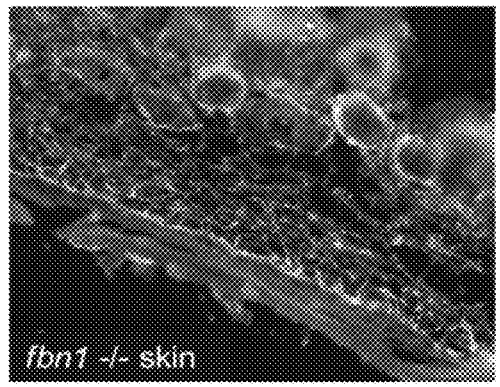
Figure 14C:
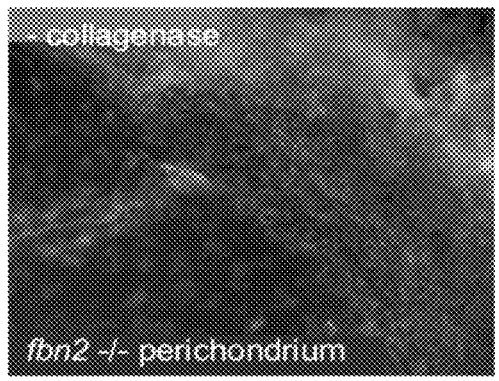
Figure 14D:
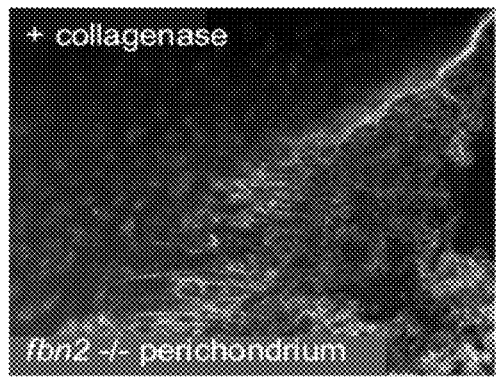

When tested by immunofluorescence on frozen sections, mAb 689 failed to yield classical fibrillin fibril staining patterns in postnatal wildtype mouse tissues (FIG. 14A). However, mAb 689 stained all early postnatal Fbn1 null tissues, yielding classic fibrillin fibril patterns and demonstrating that mAb 689 reacts well with polymeric fibrillin-2 (FIG. 14B). Therefore, in postnatal tissues, mAb 689 staining is similar to pAb 0868 fibrillin-2 antibody staining (FIG. 11).

Figure 14E:
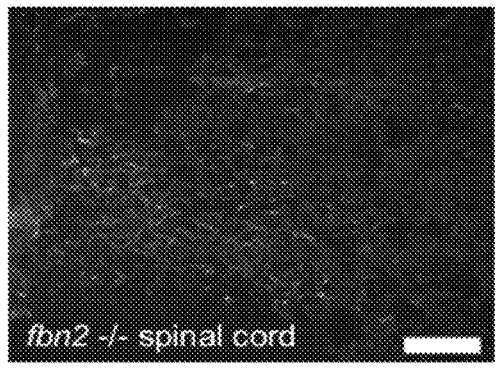
Figure 14F:
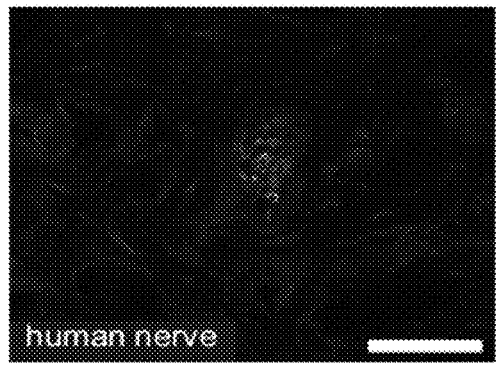

Since mAb 689 reacts well with monomeric fibrillin-1 in ELISA (FIG. 12A), polymeric fibrillin-1 microfibrils in Fbn2 null tissues were tested. mAb 689 failed to stain most Fbn2 null tissues (FIG. 14C), indicating that the mAb 689 epitope in EGF4 is unavailable in the polymerized fibrillin-1 microfibrils in most tissues. Digestion of Fbn2 null tissue sections with crude collagenase uncovered the mAb 689 epitope in the perichondrium (FIG. 14D) and in the dermis. Since the mAb 689 epitope is accessible in Fbn1 null tissue, fibrillin-2 EGF4 is exposed in the absence of fibrillin-1 (FIG. 14B). In contrast, in the absence of fibrillin-2, fibrillin-1 EGF4 remains masked. Polymerized fibrillin-1 microfibrils in the Fbn2 null spinal cord were also identified as available for binding by mAb 689, even without enzymatic unmasking (FIG. 14E). Therefore, EGF4 in fibrillin-1 is variably exposed or masked in tissues, demonstrating that tissue-specific modulation of microfibril structure can make this domain accessible.

Figure 15:
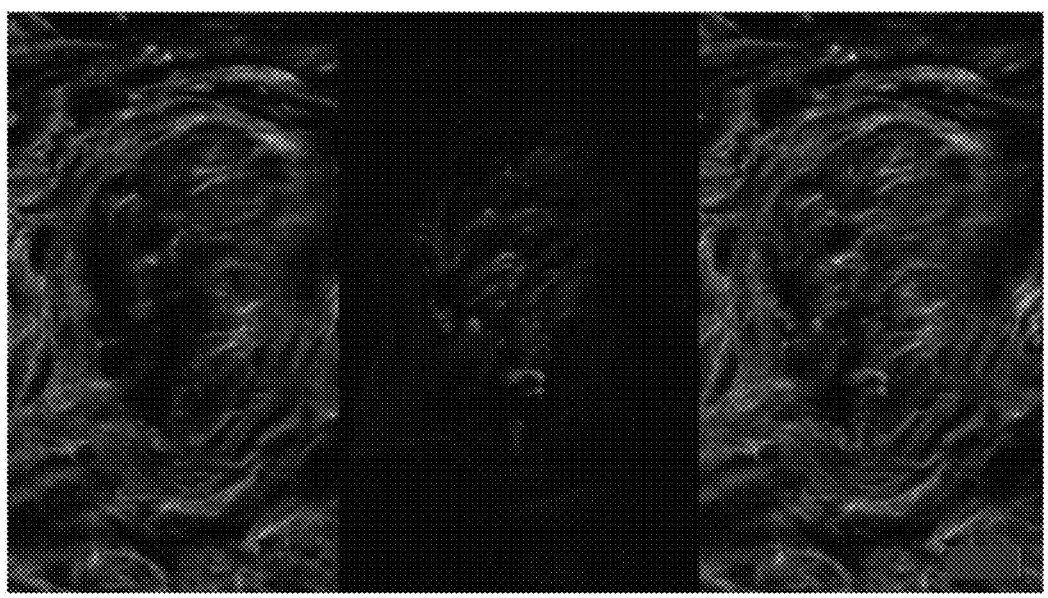
FIG. 15: Double immunofluorescence of fibrillin-1 and fibrillin-2 in human peripheral nerve. Undigested sections of 20 month human extra digit were incubated with antibodies specific for fibrillin-1 (pAb 9543) and fibrillin-2 (mAb 171). Fibrillin-1 antibodies (green, left panel) and fibrillin-2 antibodies (red, middle panel) stain discrete fibrils (merged images, right panel). Scale bar=10 μm.

To further investigate microfibrils in neuronal tissues, human 20 month postnatal digit was examined. Consistent with results showing that the cryptic mAb 689 epitope in fibrillin-1 is exposed in spinal cord (FIG. 14E), cryptic fibrillin-2 epitopes recognized by mAbs 60, 139, and 171 (FIG. 14F) were available for immunostaining of untreated peripheral nerves in the human digit. Epitopes recognized by mAbs 72 and 205 were largely masked in peripheral nerve. Double immunofluorescence clearly showed that fibrillin-1 and fibrillin-2 microfibrils in the peripheral nerve are distinct. No colocalization was observed between the green fibrillin-1 immuno-fluorescence and the red fibrillin-2 immunofluorescence (FIG. 15).

Example 1.3 Immunostaining of Fibrillin Targets in GT-8 Mice

Figure 4A:
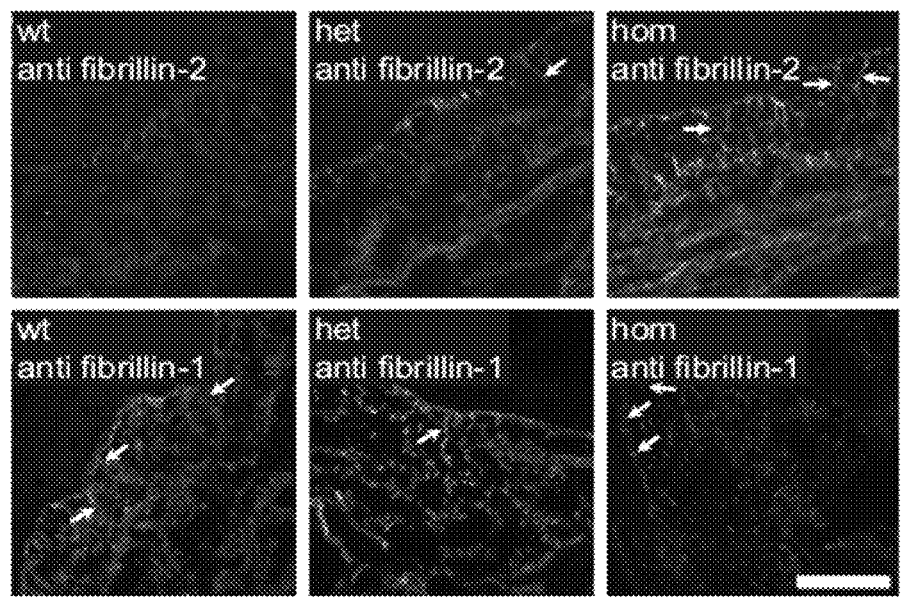
FIGS. 4A-4B. (A) P8 wildtype, heterozygous and homozygous GT-8 skin sections were stained with pAb 0868, specific for fibrillin-2, and with pAb 9543, specific for fibrillin-1. Fibrillin-2 immunostaining was barely visible in wildtype sections, but long microfibril fiber bundles (arrows), inserting perpendicularly to the dermal-epidermal junction, were revealed in heterozygous and homozygous GT-8 sections. Fibrillin-2 immunostaining was more abundant in homozygous skin sections than in heterozygous skin sections. In contrast, fibrillin-1 immunostaining showed abundant long microfibril fiber bundles (arrows) in the wildtype skin sections, but in heterozygous and homozygous sections, fibrillin-1 immunostaining appeared fragmented, with very few long fibrils at the dermal-epidermal junction. Since P3 heterozygous skin sections showed abundant long fibrillin-1 microfibril fiber bundles (FIG. 1E), P8 sections likely indicate that fragmentation of fibrillin-1 has occurred. (B) P8 wildtype, heterozygous and homozygous GT-8 sections of skeletal muscle and tendon were also examined, and similar results were obtained. Fibrillin-2 immunostaining was concealed in wildtype sections and revealed in heterozygous and homozygous skeletal muscle and tendon. In contrast, fibrillin-1 immunostaining appeared to be more fragmented in heterozygous and homozygous tissues than in the wildtype tissues. This was particularly noticeable in the skeletal muscle where fibrillin-1 immunostaining typically envelopes individual skeletal muscle fibers (arrows). Scale bars=50 μm.
Figure 4B:
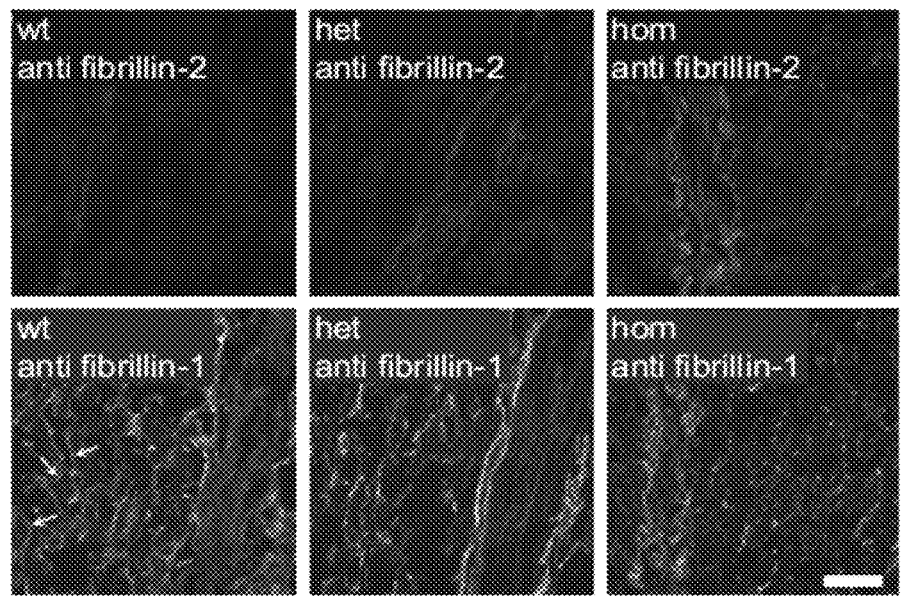

In a separate approach to determine the extent of fibrillin-2 exposure in the context of microfibrils containing mutant fibrillin-1, the extent of fibrillin-2 immunostaining revealed in GT-8/+ mouse tissues was tested. FIG. 4 shows fibrillin-2 immuno staining in P8 GT-8 heterozygous and homozygous skin (A) and in P8 GT-8 heterozygous and homozygous skeletal muscle and tendon (B) is revealed, in contrast to wildtype littermate tissue sections which are mostly negative for fibrillin-2 immunostaining. In addition, comparison of fibrillin-1 staining patterns in wildtype, heterozygous and homozygous mice evidenced increased fragmentation of fibrillin-1 patterns in heterozygous and homozygous tissues. Therefore, after microfibril assembly of mutant fibrillin-1, fragmentation of fibrillin-1 results in the unmasking of fibrillin-2, and thus fibrillin-2 is a marker of microfibril fragmentation.

Example 1.4 Detection of Circulating Fragments of Fibrillin 1 and 2 in Marfan's

Figure 5B:
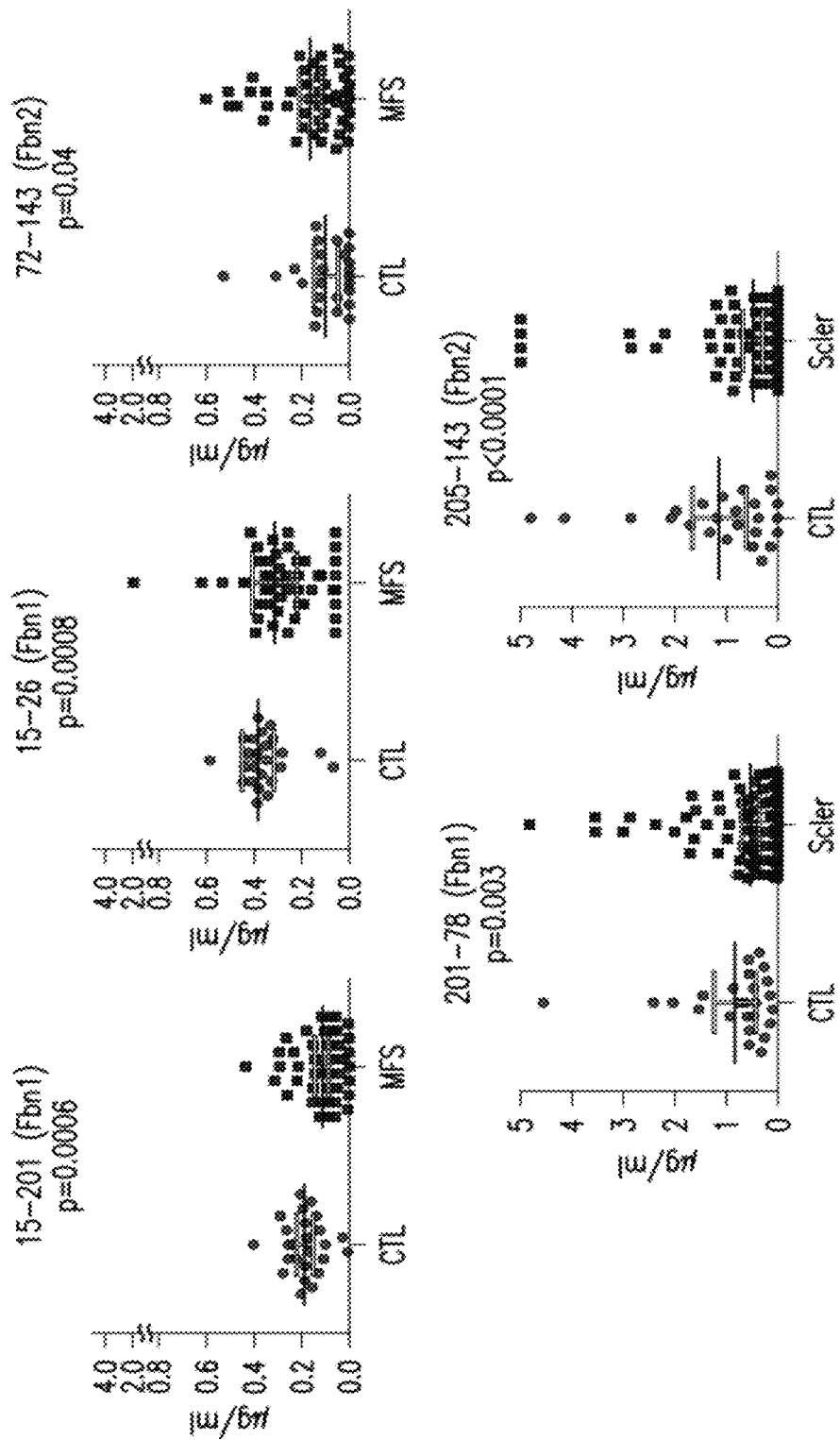
Figure 6:
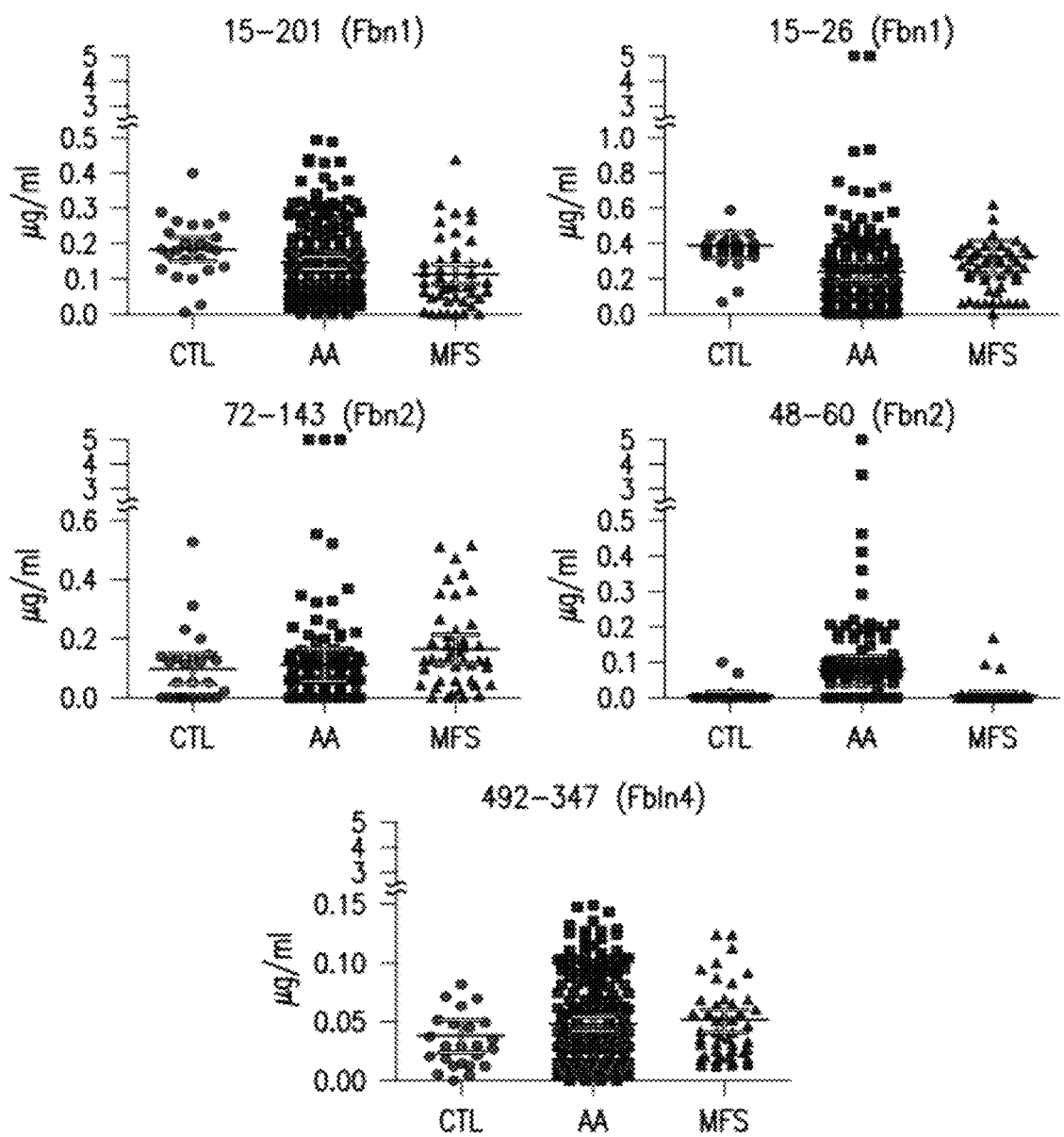
FIG. 6: Scatter plots of results from selected fibrillin-1 and fibrillin-2 sandwich ELISAs show that aortic aneurysm samples and Marfan samples displayed reduced fibrillin-1 fragments and increased fibrillin-2 fragments. The informative fibrillin-2 fragment was 48-60 in aortic aneurysm samples and 72-143 in Marfan samples. Fibulin-4 fragment 492-347 was elevated in some samples of aortic aneurysm and in some Marfan samples.

In another approach to establish that mutant fibrillin-1 targets microfibrils for proteolytic degradation, circulating fragments of fibrillin-1 and fibrillin-2 in blood samples were quantitated from individuals with Marfan's syndrome. Sandwich ELISAs were developed using several different monoclonal antibodies with defined epitopes in fibrillins (shown in FIG. 5A). Plasma from individuals with Marfan's syndrome showed significantly reduced amounts of fibrillin-1 fragments, and increased amounts of fibrillin-2 fragments, when compared to control plasma (FIG. 5B). In contrast, when fragments of fibrillins were measured in blood samples from individuals with scleroderma, fibrillin-1 fragments and fibrillin-2 fragments were both reduced when compared to control samples. Table 1 shows values for all fibrillin-1 and fibrillin-2 fragments detected by current combinations of antibody pairs, including the pairs that showed no differences between controls and test groups.

TABLE 1

|      | Fragment | Control (n = 25) | MFS (n = 48) | Scleroderma (n = 115) |
|------|----------|------------------|--------------|----------------------|
| Fbn1 | 15-201   | 0.19 +/− 0.08    | 0.12 +/− 0.1 | 0.18 +/− 0.09 |
|      | 15-26    | 0.39 +/− 0.16    | 0.32 +/− 0.32| 0.4 +/− 0.27 |
|      | 15-78    | 0.37 +/− 0.2     | 0.34 +/− 0.28| 0.4 +/− 0.26 |
|      | 201-78   | 0.84 +/− 0.97    | 0.96 +/− 0.95| 0.54 +/− 0.82 |
| Fbn2 | 205-143  | 1.1 +/− 1.2      | 1 +/− 1      | 0.48 +/− 1 |
|      | 72-143   | 0.1 +/− 0.12     | 0.16 +/− 0.16| 0.16 +/− 0.29 |
|      | 48-60    | 0.007 +/− 0.02   | 0.007 +/− 0.02| 0.028 +/− 0.06* |

Table 1 shows the fibrillin fragment concentration, quantitated using sandwich ELISAs for the indicated fragments (named for the antibody pair used). Data are expressed as mean concentration in µg/ml+/−s.d. The asterisk indicates that only 44 samples were tested for this fragment. It is of interest that the informative fragments for Marfan's syndrome were uninformative for scleroderma. As expected, as was originally predicted for two-site sandwich ELISAs with monoclonal antibodies (Uotila 1981), the exquisite specificities of monoclonal antibodies for different fibrillin epitopes can be exploited to identify fragments of biological significance in Marfan's syndrome compared to other diseases.

In vitro enzymatic unmasking experiments as well as in vivo analyses of Fbn1 null mice indicate that fibrillin-2 is normally masked in microfibrils by fibrillin-1. Analyses of microfibrils in Fbn1 GT-8 mutant mouse skin show fragmentation of fibrillin-1 immunostaining, reminiscent of our original findings of fragmented fibrillin-1 staining in skin biopsies from individuals with the Marfan's syndrome (Hollister 1990), as well as increased fibrillin-2 immunostaining. Based on these data, mutant fibrillin-1 targets fibrillin-1 for degradation, revealing fibrillin-2. By quantitating circulating fragments of fibrillins in humans, it was discovered a Marfan signature profile consisting of reduced fibrillin-1 and increased fibrillin-2 fragments. Studies of individuals with scleroderma as well as other non-Marfan populations demonstrate that concentrations of fibrillin-2 fragments are usually very low. This data shows that incorporation of certain mutant fibrillin-1 proteins into microfibrils targets fibrillin-1 first, since it is on the surface of the microfibril, for degradation and then, as fibrillin-1 is removed from the surface of the microfibril, exposing fibrillin-2, fibrillin-2 is also degraded.

Example 2: Statistical Analysis Relating to Elastic Fiber Fragment Profiling

Classification of fibrillin-1 and fibrillin-2 fragment concentrations into groups is accomplished with the k-means clustering procedure (FASTCLUS in SAS). The k-means procedure uses values called Euclidean distance to place individuals from the entire study sample into mutually exclusive groups that maximize between-group variation and minimize with-in group variation. The advantage of k-means clustering is that it does not depend on the user to decide a specific number of clusters—or groups—to be used. To determine the appropriate number of clusters several steps are employed. Initially, the FASTCLUS procedure is permitted to identify the number of potential clusters, which is the default setting in the software. After inspecting the cluster summary output statistics and plots showing the spread of the clusters, additional analyses that vary the initial seed and the numbers of clusters are performed. The number of observations in the different clusters are examined in order to avoid clusters comprised of small numbers of observations or of just one observation with an extreme value. If clusters with a small number of patients are formed, the fibrillin concentrations are examined to determine if patients with extreme values are identified. These observations can be eliminated and the cluster selection is repeated. Once the appropriate number of clusters is identified in light of the data, the distributions of the fibrillin fragment concentrations in each cluster is determined. This enables the characterization of the cluster according to levels of the fibrillin fragment concentrations.

As a last step in these descriptive analyses, distributions of the patient and clinical variables are examined according to the cluster variable using one-way ANOVA for continuous variables or chi-square and Fisher's exact tests (if appropriate) for categorical variables.

Multivariable Analyses: The categorical variable defining the clusters will be the primary independent variable. As is customary, indicator variables for the clusters will be created for use in statistical modeling. The group containing the highest proportion of non-Marfan patients is considered the 'referent cluster.' Logistic regression is used to determine the frequency with which Marfan patients are represented in each cluster category relative to the frequency of non-Marfan patients. The association produced by the logistic model is the odds ratio (OR). OR greater than 1.0 indicates the frequency of the cluster of interest (e.g. low fibrillin-1 and high fibrillin-2 fragment concentrations) is greater among the Marfan patients than it is among the non-Marfan patients; OR less than 1.0 indicates that the frequency of the cluster of interest is lower among the Marfan patients compared to the non-Marfan patients.

Next, the variable for fibulin-4 is added in order to establish this molecule has a role in aneurysm etiology independent of its association with fibrillin-1. Fibulin-4 is evaluated as a continuous term or as indicator terms for quartiles. In the next step, potential confounding factors are assessed systematically. Candidates are those that biologically could be considered important, such as age, along with those that differed in the descriptive analyses by Marfan status and/or by cluster (at p-value of ≤0.15). Candidates are entered one at a time into the model. If entry of a variable changes the OR by at least 10% (18), it is retained. When necessary, potential confounding factors that are highly correlated are distinguished by evaluating which changes the OR to the greatest extent. If the level of confounding by two candidates is similar, the best fitting variable is retained. After confounding has been assessed, the other remaining variables are fitted one at a time. Any that are determined to be confounders in the presence of other variables already in the model or that contribute to model fit are retained.

Example 3: Profiling Elastic Fiber Fragments Over Time as Indicators of Disease Progression Circulating elastic fiber and microfibril fragments are monitored over time in genetically mutant mice that develop aortic aneurysms. The Fbn1 mutant mouse strain GT-8, described above, carries the mutant Fbn1 allele in all cells and is maintained on the C57/Bl6 background. GT-8/+ males are breed to wildtype females, generating ~50% wildtype and ~50% heterozygous pups in every litter. Mice of both genotypes are exsanguinated at 13 timepoints: P5, P10, P15, and monthly from 1 to 10 months of age. A minimum of 10 mice of each genotype are analyzed at these 13 timepoints. Aortic disease in each sacrificed mouse is scored according to numbers of breaks in the aortic root elastic lamellae, whether breaks cross the width of the wall (without intact lamellae between breaks), and whether there is infiltration of blood cells into the smooth muscle media. Micrographs of entire root sections are blinded as to genotype and scored from 1-10, with 1 being a normal aortic root and 10 showing dissection with blood cell infiltration. Each individual mouse is measured for concentrations of fibrillin-1 and fibrillin-2 fragments and given a score from 1-10. Mice are visually examined for the association between release of fibrillin-1 and -2 fragments with aneurysm score over time with restricted cubic splines, a non-parametric approach. The splines enable the determinination of the shape of the relation in the two genotypes over time without assumptions regarding the underlying distributions of the variables. Linear regression analysis is used to predict the mean increases in fibrillin-1 and fibrillin-2 fragment concentrations that predict an increase in the aneurysm score.

In order to establish that inhibitors of progression of aneurysm attenuate concentrations of circulating fibrillin-1 and fibrillin-2 fragments, mice are treated with losartan and with doxycycline. Losartan (0.6 g/l) or doxycycline (100 mg/kg/day) is administered in the drinking water from P1, and control litters are given regular drinking water. The same timepoints and histological scoring described above is utilized. The effect of treatment on fragment release is evaluated with a test of means from fixed effects models.

Two sandwich ELISAs are established that can detect mouse fibrillin-1, using affinity purified pAb 9543 (generated using rF11, the recombinant N-terminal half of fibrillin-1) on recombinant subdomains of rF11 coupled to Sepharose. The rF23/rF20 fibrillin-1 fragment assay targets the region of fibrillin-1 that are interrogated in humans, above. Plasma samples from P6 littermate wildtype, heterozygous, and homozygous mutants, 3 month old littermate wildtype and heterozygous mutants (homozygous mutants are unavailable at older ages because they die between P9 and P16), 6 month old littermate wildtype and heterozygous mutants, and 7 month old littermate wildtype and heterozygous mutants are tested for circulating fibrillin-1 fragments. Circulating fibrillin-1 fragments in 3 littermate P6 heterozygous mutants (4.27 ng/ml; 3.01 ng/ml; 3.87 ng/ml) and 1 P6 homozygous mutant (7.18 ng/ml) are detected, while they are undetectable in the P6 wildtype littermate. At 3 months of age, circulating fibrillin-1 fragments are detected in 1 female heterozygous mutant (2.69 ng/ml) but are undetectable in 1 littermate wildtype female, as well as in 1 littermate heterozygous male and 1 littermate wildtype male. Fragments are undetectable in 1 wildtype and 1 heterozygous mutant at 6 months of age and at 7 months of age. These results are consistent with fibrillin-1 fragments increasing at early timepoints and decreased at later time points, as aortic disease is progressing.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A method of treatment of aortic aneurysm, wherein the method comprises monitoring the profile of fibrillin 1 and fibrillin 2 fragments present in a subject by an enzyme-linked immunosorbent assay, and providing an interventional therapy when the profile shows an initial increase of fibrillin 1, followed by a decrease of fibrillin 1 and an increase of fibrillin 2, indicating progression of aortic aneurysm,
   wherein the interventional therapy comprises: a surgical intervention; administration of antibiotic prophylaxis; administration of losartan; or administration of a beta-blocker, wherein said monitoring is performed on a sample obtained from the subject and the sample is selected from the group consisting of blood, serum, plasma, urine, saliva, sputum, mucus, semen, amniotic fluid, mouth wash and bronchial lavage fluid.

2. The method of claim 1, wherein the sample is a blood sample.

3. The method of claim 1, wherein the enzyme-linked immunosorbent assay is a sandwich ELISA.

4. The method of claim 3, wherein antibody pairs are used to profile fibrillin 1 and fibrillin 2.

5. The method of claim 4, wherein the antibodies are selected from the group consisting of mAb 15, 26, 48, 60, 69, 72, 78, 143, 201, and 205.

6. The method of claim 1, wherein the interventional therapy comprises a surgical intervention.

7. The method of claim 1, wherein the interventional therapy comprises administration of antibiotic prophylaxis.

8. The method of claim 1, wherein the interventional therapy comprises administration of losartan.

9. The method of claim 1, wherein the interventional therapy comprises administration of a beta-blocker.

10. The method of claim 1, wherein the interventional therapy comprises administration of losartan and administration of a beta-blocker.

* * * * *

SEQUENCE LISTING

<160> NUMBER OF SEQ ID NOS: 13

<210> SEQ ID NO 1
<211> LENGTH: 41
<212> TYPE: PRT
<213> ORGANISM: Homo sapiens

<400> SEQUENCE: 1

Val Thr Asp Tyr Cys Gln Leu Val Arg Tyr Leu Cys Gln Asn Gly Arg
1               5                   10                  15

Cys Ile Pro Thr Pro Gly Ser Tyr Arg Cys Glu Cys Asn Lys Gly Phe
            20                  25                  30

Gln Leu Asp Ile Arg Gly Glu Cys Ile

-continued 35                  40

<210> SEQ ID NO 2
<211> LENGTH: 41
<212> TYPE: PRT
<213> ORGANISM: Homo sapiens

<400> SEQUENCE: 2

Thr Ile Asp Ile Cys Lys His His Ala Asn Leu Cys Leu Asn Gly Arg
1               5                   10                  15

Cys Ile Pro Thr Val Ser Ser Tyr Arg Cys Glu Cys Asn Met Gly Tyr
            20                  25                  30

Lys Gln Asp Ala Asn Gly Asp Cys Ile
        35                  40

<210> SEQ ID NO 3
<211> LENGTH: 40
<212> TYPE: PRT
<213> ORGANISM: Homo sapiens

<400> SEQUENCE: 3

Thr Ile Asp Ile Cys Arg His Phe Thr Asn Leu Cys Leu Asn Gly Arg
1               5                   10                  15

Cys Leu Pro Thr Ser Ser Tyr Arg Cys Glu Cys Asn Val Gly Tyr Thr
            20                  25                  30

Gln Asp Val Arg Gly Glu Cys Ile
        35                  40

<210> SEQ ID NO 4
<211> LENGTH: 23
<212> TYPE: DNA
<213> ORGANISM: Artificial Sequence
<220> FEATURE:
<223> OTHER INFORMATION: synthetic DNA primer sequence

<400> SEQUENCE: 4
ccgtggaatc taaaaccttg gag                                           23

<210> SEQ ID NO 5
<211> LENGTH: 22
<212> TYPE: DNA
<213> ORGANISM: Artificial Sequence
<220> FEATURE:
<223> OTHER INFORMATION: synthetic DNA primer sequence

<400> SEQUENCE: 5
tgggaatgat gtggtgagag cc                                            22

<210> SEQ ID NO 6
<211> LENGTH: 24
<212> TYPE: DNA
<213> ORGANISM: Artificial Sequence
<220> FEATURE:
<223> OTHER INFORMATION: synthetic DNA primer sequence

<400> SEQUENCE: 6
gtgggttcca ttagagcatt catc                                          24

<210> SEQ ID NO 7
<211> LENGTH: 24
<212> TYPE: DNA
<213> ORGANISM: Artificial Sequence
<220> FEATURE:
<223> OTHER INFORMATION: synthetic DNA primer sequence

```
<400> SEQUENCE: 7
ggtgagagcc tgtattgttt cctc                                          24

<210> SEQ ID NO 8
<211> LENGTH: 22
<212> TYPE: DNA
<213> ORGANISM: Artificial Sequence
<220> FEATURE:
<223> OTHER INFORMATION: synthetic DNA primer sequence

<400> SEQUENCE: 8
ttggaatgac aggctgtggc ac                                            22

<210> SEQ ID NO 9
<211> LENGTH: 21
<212> TYPE: DNA
<213> ORGANISM: Artificial Sequence
<220> FEATURE:
<223> OTHER INFORMATION: synthetic DNA primer sequence

<400> SEQUENCE: 9
ttcgctgtgt ttctacaagg c                                             21

<210> SEQ ID NO 10
<211> LENGTH: 20
<212> TYPE: DNA
<213> ORGANISM: Artificial Sequence
<220> FEATURE:
<223> OTHER INFORMATION: synthetic DNA primer sequence

<400> SEQUENCE: 10
tgtctccagc cctacttcgt                                               20

<210> SEQ ID NO 11
<211> LENGTH: 20
<212> TYPE: DNA
<213> ORGANISM: Artificial Sequence
<220> FEATURE:
<223> OTHER INFORMATION: synthetic DNA primer sequence

<400> SEQUENCE: 11
cctcggagta tttcctgctg                                               20

<210> SEQ ID NO 12
<211> LENGTH: 24
<212> TYPE: DNA
<213> ORGANISM: Artificial Sequence
<220> FEATURE:
<223> OTHER INFORMATION: synthetic DNA primer sequence

<400> SEQUENCE: 12
ggagaggcta ttcggctatg actg                                          24

<210> SEQ ID NO 13
<211> LENGTH: 24
<212> TYPE: DNA
<213> ORGANISM: Artificial Sequence
<220> FEATURE:
<223> OTHER INFORMATION: synthetic DNA primer sequence

<400> SEQUENCE: 13
ctcttcgtcc agatcatcct gatc                                          24
```